US012390646B2

(12) United States Patent
Nesbitt et al.

(10) Patent No.: US 12,390,646 B2
(45) Date of Patent: Aug. 19, 2025

(54) IMPLANTABLE MEDICAL DEVICES

(71) Applicant: INSPIRE MEDICAL SYSTEMS, INC., Golden Valley, MN (US)

(72) Inventors: Nicholas Nesbitt, Minneapolis, MN (US); Kevin Verzal, Lino Lakes, MN (US); David Dieken, Minneapolis, MN (US); John Rondoni, Plymouth, MN (US); Christopher Thorp, Minneapolis, MN (US); Douglas Murphy, Golden Valley, MN (US)

(73) Assignee: INSPIRE MEDICAL SYSTEMS, INC., Golden Valley, MN (US)

( * ) Notice: Subject to any disclaimer, the term of this patent is extended or adjusted under 35 U.S.C. 154(b) by 378 days.

(21) Appl. No.: 17/539,916

(22) Filed: Dec. 1, 2021

(65) Prior Publication Data

US 2023/0166113 A1    Jun. 1, 2023

Related U.S. Application Data

(60) Provisional application No. 63/120,313, filed on Dec. 2, 2020.

(51) Int. Cl.
*A61N 1/36* (2006.01)
*A61N 1/05* (2006.01)

(52) U.S. Cl.
CPC .......... *A61N 1/36178* (2013.01); *A61N 1/05* (2013.01); *A61N 1/3611* (2013.01); *A61N 1/36192* (2013.01); *A61N 1/36196* (2013.01)

(58) Field of Classification Search
CPC .... A61N 1/36178; A61N 1/05; A61N 1/3611; A61N 1/36192; A61N 1/36196;
(Continued)

(56) References Cited

U.S. PATENT DOCUMENTS 7,742,810 B2    6/2010  Moffitt et al.
8,036,754 B2   10/2011  Lee et al.
(Continued)

FOREIGN PATENT DOCUMENTS

WO         2020128748 A1    6/2020

OTHER PUBLICATIONS

Ungar IJ, Mortimer JT, Sweeney JD. Generation of unidirectionally propagating action potentials using a monopolar electrode cuff. Ann Biomed Eng. 1986; 14(5):437-50. doi: 10.1007/BF02367364. Pmid: 3789489.*
(Continued)

*Primary Examiner* — Mallika D Fairchild
(74) *Attorney, Agent, or Firm* — DICKE, BILLIG & CZAJA, PLLC

(57) ABSTRACT

One example of an implantable medical device includes an output signal driver, a first electrode, a second electrode, and a controller. The output signal driver is configured to generate stimulation pulses to stimulate a nerve within a patient. The first electrode is coupled to the output signal driver. The second electrode is coupled to the output signal driver. The controller is configured to control the output signal driver to selectively apply between the first electrode and the second electrode a first pulse train and a second pulse train interleaved with the first pulse train.

26 Claims, 13 Drawing Sheets

(58) Field of Classification Search
CPC ............. A61N 1/0551; A61N 1/36007; A61N 1/36171; A61N 1/36175
See application file for complete search history.

(56) References Cited

U.S. PATENT DOCUMENTS

| | | | | |
|---|---|---|---|---|
| 8,509,901 | B2* | 8/2013 | Tehrani | A61N 1/36132 607/42 |
| 9,375,575 | B2 | 6/2016 | Moffitt et al. | |
| 10,744,327 | B2 | 8/2020 | Bonnet et al. | |
| 2003/0204223 | A1* | 10/2003 | Leinders | A61N 1/36071 607/48 |
| 2004/0243182 | A1* | 12/2004 | Cohen | A61N 1/36007 607/2 |
| 2013/0030498 | A1* | 1/2013 | Karamanoglu | A61N 1/36139 607/42 |
| 2014/0277281 | A1* | 9/2014 | Grandhe | A61N 1/36153 607/59 |
| 2017/0246456 | A1* | 8/2017 | Tyler | A61N 1/36103 |
| 2018/0272133 | A1* | 9/2018 | Kibler | A61N 1/36071 |
| 2021/0052893 | A1 | 2/2021 | Suri et al. | |
| 2021/0093868 | A1 | 4/2021 | Hunsberger | |

OTHER PUBLICATIONS

Goodall Article—Eleanor V. Goodall et al., "Position-Selective Activation of Peripheral Nerve Fibers with a Cuff Electrode", vol. 43, Aug. 1996, pp. 851-856. Copyright 1996, IEEE Transactions On Biomedical Engineering (6 pages).

* cited by examiner

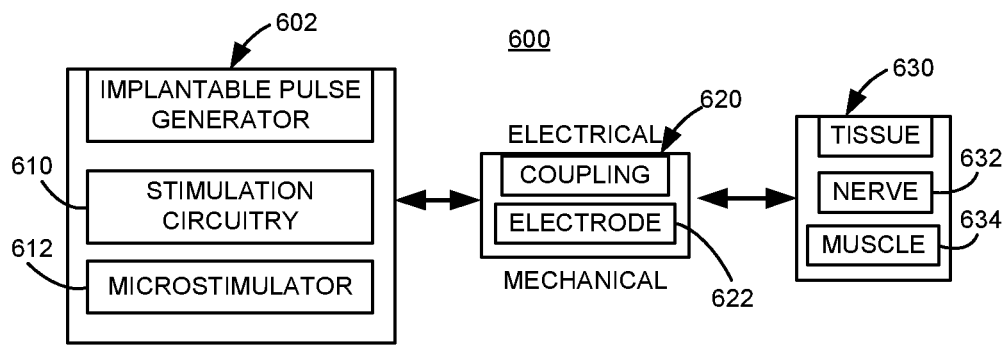
FIG. 6
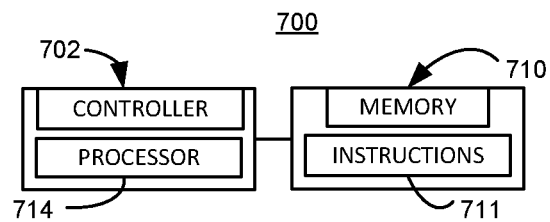
FIG. 7A
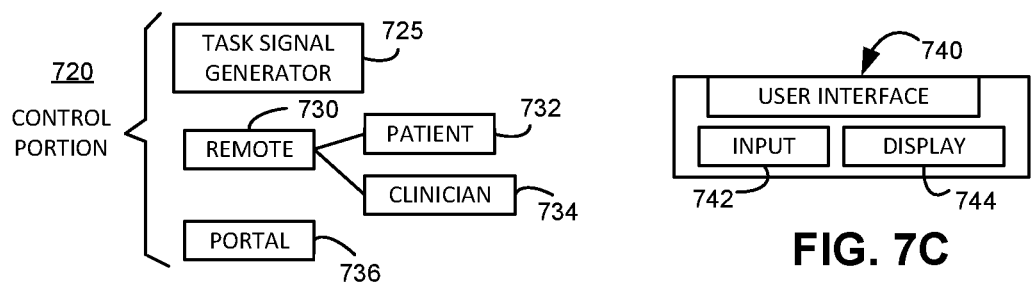
FIG. 7B
FIG. 7C

IMPLANTABLE MEDICAL DEVICES

CROSS-REFERENCE TO RELATED APPLICATIONS

This application claims the benefit of the filing date of U.S. Provisional Application Ser. No. 63/120,313, filed Dec. 2, 2020 and entitled "Implantable Medical Devices," the entire teachings of which are incorporated herein by reference.

BACKGROUND

Medical devices, such as implantable medical devices, may include a stimulation engine to provide therapeutic electrical pulses to tissue within a patient.

BRIEF DESCRIPTION OF THE DRAWINGS

FIG. 6 is a block diagram schematically illustrating one example of an implantable medical device including example stimulation circuitry.

FIG. 7A is a block diagram schematically illustrating an example control portion.

FIG. 7B is a block diagram schematically illustrating various example control portion arrangements.

FIG. 7C is a block diagram schematically illustrating an example user interface.

DETAILED DESCRIPTION

Figure 1A:
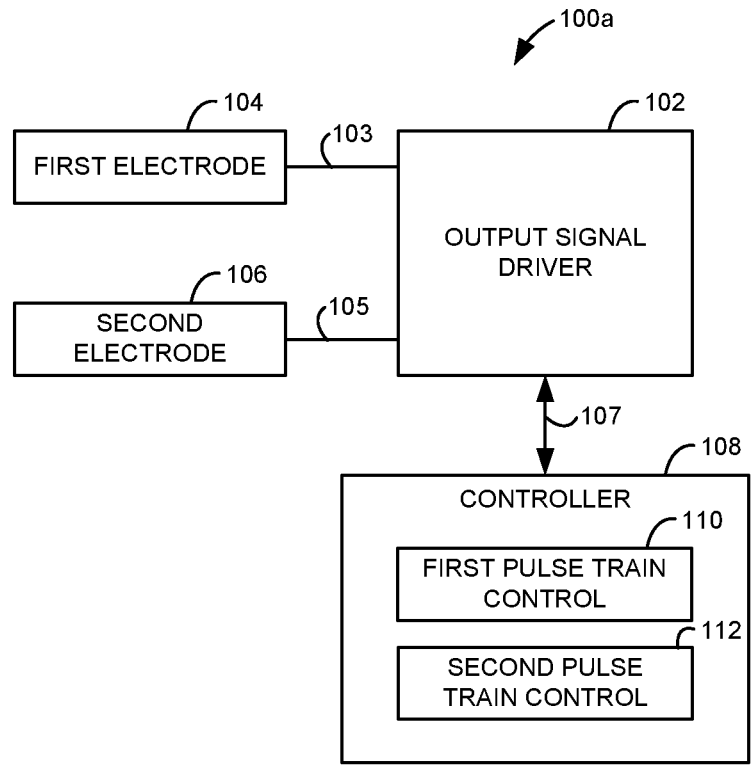
FIGS. 1A-1B are block diagrams schematically illustrating examples of an implantable medical device.

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense. It is to be understood that features of the various examples described herein may be combined, in part or whole, with each other, unless specifically noted otherwise.

At least some examples of the present disclosure are directed to stimulation circuitry for providing stimulation therapies. In some examples, the stimulation therapy may be adapted to provide peripheral nerve stimulation, which in some examples may include treatment of sleep disordered breathing (SDB). The sleep disordered breathing may include obstructive sleep apnea, central sleep apnea, and/or multiple-type sleep apnea. In doing so, the stimulation may be directed to tissue(s) which at least partially control upper airway patency, such as those nerves innervating at least the muscles of the tongue, the palate, and/or related upper airway musculature. Such nerves include, but are not limited to, the hypoglossal nerve, the protrusors of the distal hypoglossal nerve, the retractors and protrusors of the proximal hypoglossal nerve, and ansa cervicalis-related nerves such as various locations along the ansa-cervicalis and/or branching from the ansa cervicalis. In some such examples, the stimulation therapy may be adapted to be applied directly to musculature related to controlling upper airway patency. In some examples, the stimulation therapy may be directed to stimulation of the phrenic nerve and/or diaphragm to treat central sleep apnea and/or treat multiple-type apnea.

In some examples, the peripheral nerve stimulation may be implemented to treat incontinence, including one or both of urinary incontinence and fecal incontinence of a patient, or other pelvic disorders. At least some such examples include implanting an electrode to deliver a nerve stimulation signal to one or more nerves or nerve branches to activate a corresponding external sphincter, such as a branch of the pudendal nerve that activates the external urethral sphincter and/or the external anal sphincter. In some examples, such stimulation therapies also may be adapted to directly stimulate related muscles.

In some examples, a stimulation therapy may be implemented as cardiac therapy, i.e. therapies to treat various cardiac tissues and may involve stimulation of nerve targets and/or related muscle targets.

In some examples, a stimulation therapy may be implemented as treatment of the disorders and dysfunctions of the central nervous system (CNS).

In providing any of the above-described example therapies, an example stimulation circuitry may form part of a medical device (e.g., an implantable medical device), which may include an implantable pulse generator. At least some various example implementations are further described below.

At least some of the above-described examples of stimulation of physiological targets may be implemented according to a stimulation circuitry, such as the output signal driver as further described and illustrated below in association with FIGS. 1A-7C. However, it will be understood that the various examples described in association with FIGS. 1A-7C may also be applicable to stimulation therapies other than, or in addition to, the above-described examples.

Among other attributes, at least some example stimulation circuitry of the present disclosure includes electrode configurations and stimulation burst methods that optimize the effectiveness and selectivity of recruiting those nerve fascicles with positive therapeutic effect while minimizing stimulation spread to non-therapeutic regions of local nerves and musculature. The example stimulation circuitry provides improved control over the tuning of stimulation, allowing adjustment of those parameters most relevant to a therapy, such as upper airway stimulation (UAS) to stimulate motor nerves innervating the tongue and soft palate to treat obstructive sleep apnea (OSA), while avoiding recruitment of those motor nerves (e.g., retractor branches of the hypoglossal nerve) with benign or antagonistic effects on therapeutic outcomes.

With regard to the examples of the present disclosure, each nerve includes at least one axon and may contain many axons. In some instances, an axon may sometimes be referred to as a nerve fiber or axonal fiber. Within a nerve, each axon is surrounded by a layer of connective tissue called the endoneurium. Some axons (i.e., nerve fibers) may be bundled together into groups called fascicles, such that reference to a fascicle or nerve fascicle will be understood to refer to a bundle or group of axons (or nerve fibers) within a nerve. In addition, the term afferent is generally used to refer to those nerve fibers (i.e., axons) that receive information from sensory organs, which is then transmitted to the central nervous system. An afferent nerve fiber may sometimes be referred to as a sensory nerve fiber. However, the term efferent is generally used to refer to those nerve fibers that send impulses from the central nervous system to peripheral body portions (e.g., legs, arms, etc.) and organs. An efferent nerve fiber may sometimes be referred to as a motor nerve fiber, such as when the peripheral body portion comprises muscles innervated by the particular efferent nerve fiber. In just one example, in the context of treating sleep disordered breathing, stimulation of the hypoglossal nerve may be understood to refer to stimulation of efferent nerve fibers or efferent nerve fascicles (i.e., group(s) of efferent nerve fibers) which cause contraction of the genioglossus muscle. In such examples, in which the efferent nerve fibers comprise nerve fibers which innervate protrusors of the genioglossus muscle, such stimulation may result in increasing upper airway patency to alleviate obstructive sleep apnea.

Some therapeutic UAS implementations may have some difficulties as follows:

1) Various devices deliver electric stimulation to physiologic systems for therapeutic effect. Such devices generally suffer from side effects due to the spread of electric current and the off-target delivery of stimulation. Off-target delivery of stimulation or other undesirable effects and implications that may be observed in patients implanted with UAS include, but are not limited to:

a) Rare phenomenon in which patients hear (i.e., auditory sensation) stimulation. The auditory sensation in patients may be due to coupling with sensory facial nerves or coupling with muscle groups that elicit an audible response. The auditory sensation increases patient dissatisfaction with therapy.

b) Nerves innervating the muscles that open the airway are embedded within or are near other muscle groups. Current spread can have counter-productive impact if stimulation spreads to nerves or muscles antagonistic to the therapeutic targets.

c) In the case of UAS, it is theorized that muscle response may sometimes be elicited directly, near the electrode(s), rather than via recruitment of motor nerves as intended. The direct recruitment of retractor (motor) muscles or the nerve fascicles that innervate them may result in counter-active muscle contraction that negatively impacts the predictability and effectiveness of therapy. There may also be nerve-based recruitment of retractor muscles that negatively impacts the predictability and effectiveness of therapy.

d) Other muscle groups without direct therapeutic impact may also be recruited, with various side effects, but most noticeably an increased likelihood of patient arousal.

e) Off target elicitation of action potentials in sensory nerves may cause patient discomfort.

2) Placing an electrode(s) precisely at the correct target location may be challenging. Variable and/or imperfect placement of an electrode(s) increases the likelihood that a simple and/or minimally adjustable stimulation pattern will induce off target effects. Interweaving and inhomogeneity of fascicles within the nerve means that surgical placement and technique may have a large impact on the effectiveness of the implanted system and result in greater variance in patient response.

3) A tension may exist between efficacy and arousal. While a higher stimulation amplitude generally results in greater nerve recruitment and therapeutic effect, increases in stimulation amplitude may sometimes increase the risk of patient discomfort or arousal from sleep. Amplitude adjustments provide an effective parameter for therapy adjustment but come with this tradeoff.

4) The membrane of the axon imposes directionality of an action potential by using a refractory period of hyperpolarization (which trails the propagating action potential); however, bidirectional elicitation of action potentials may result when stimulation occurs somewhere along the axon body (i.e., not originating from the cell body). The impact of these "backwards" propagating signals is not well understood, but evidence suggests undesirable effects in other stimulating devices due to this effect.

At least some examples of the present disclosure may address at least the above-mentioned difficulties as follows:

I) In some examples, adjustment of stimulation amplitude, duty cycle, pulse frequency, or burst duration may be made by the patient or physician. A burst is a collection of pulses that may have its own duration, number of pulses, frequency, duty cycle, etc. While greater stimulation amplitude may increase therapy effectiveness, a balance between effectiveness and patient arousal and patient comfort may be considered. In some examples, stimulation pulse time or duty cycle can also be adjusted by a clinician.

II) In some examples, an UAS system may utilize different modes for stimulation delivery. Two such modes are a pseudo-tripolar cuff configuration (i.e., voltages applied between stimulation electrodes local to the stimulation target; two of these electrodes are linked, or "shorted", to prevent current leakage out of the cuff) and a "distal" mode (i.e., voltage applied between an electrode at the nerve target and a distant electrode). Little control is given over the path current actually follows through the anisotropic environment of tissue due to simple and/or minimally adjustable pulse patterns, electrode configurations, etc.

III) Refining surgical methods and training results in improved electrode placement and more effective delivery of therapy. In worst case situations of patient non-response to therapy, implanted devices may be explanted.

The present disclosure may expand on item (I) above in that at least some example systems and methods disclosed herein may implement greater control over the paths of current spread through tissue (e.g., current steering) and over the time-course pattern of a stimulation burst (e.g., interleaving pulse patterns). This may allow tuning of parameters relevant to the delivery of UAS for more effective tuning of therapy for increased therapeutic efficacy and minimization of patient arousal.

The present disclosure may expand on item (II) above in that at least some examples of the systems and methods disclosed herein may accommodate various electrode configurations designed to optimize the selectivity of nerve fascicles that innervate muscles with therapeutic effect. The combination of electrode configuration and stimulation paradigm (presented by at least some examples of the present disclosure) is designed to be suited to UAS and provides a means of fine-tuning stimulation parameters for greater efficacy. Asymmetrical electrode placement, asymmetrical stimulation amplitudes across electrodes, greater control over pulse shape, and other strategies detailed in at least some examples of the present disclosure may enable therapy to be delivered to therapeutic targets with greater spatial specificity and with greater control over the directionality of elicited action potentials.

The present disclosure expands on item (III) above in that at least some example systems and methods disclosed herein provide adjustments for tuning spatial distribution of stimulation and the selectivity of nerve recruitment, such that a greater level of tuning is provided via programmatic control. This relaxes the stringency on surgical technique, as stimulation can be adjusted to accommodate a wider range of surgical placement.

In summary, means of adjusting the stimulation delivered to nerves that innervate the tongue and soft palate offer limited adjustment over the specificity of nerve recruitment. In sharp contrast, at least some example systems and methods of the present disclosure include stimulation adjustments to provide greater selectivity based on nerve type, axon diameter, etc. and greater spatial specificity for more targeted delivery of stimulation to the appropriate nerve fascicles and avoidance of delivery of stimulation to off-target fascicles or nearby muscles.

In some examples, the present disclosure provides a stimulation architecture that is designed for tuning and optimization of UAS. At least some aspects of the present disclosure addresses problems specific to the delivery of UAS, such as minimizing current spread to facial nerves, selective recruitment of motor fascicles with therapeutic effect, and control over the unique stimulation vectors followed in this body region. A greater specificity of nerve recruitment may allow for a lower amplitude of stimulation to be delivered with the same therapeutic impact, reducing the power draw of stimulation and decreasing the likelihood of patient arousal. At least some example stimulation architecture disclosed herein also may allow greater control over the path current follows through tissue, allowing greater selectivity and lower amplitudes of stimulation to be utilized. In addition, the probability of revision surgery may be reduced, as more adjustment to therapy can be made without modifying the implant.

At least some example stimulation architecture disclosed herein may provide more effective delivery of UAS by implementing stimulation burst patterns that are better optimized to the therapeutic target and by implementing methods for greater control of the pathways followed by current, minimizing off-target effects and improving recruitment of target nerves. The stimulation burst patterns and methods for greater control of the pathways followed by current may also be implemented to provide more effective delivery of stimulation to other nerve targets and/or related muscle targets as described herein.

While the output signal driver described below is disclosed as being part of a medical device, such as an implantable medical device, the output signal driver is also applicable to non-implantable medical devices (e.g., trial stimulator, temporary stimulator, TENS, etc.).

FIG. 1A is a block diagram schematically illustrating one example of an implantable medical device 100a. Implantable medical device 100a includes an output signal driver 102, a first electrode 104, a second electrode 106, and a controller 108. The output signal driver 102 is electrically coupled to the first electrode 104 through a signal path 103 and to the second electrode 106 through a signal path 105. The output signal driver 102 is electrically coupled to the controller 108 through a signal path 107. Controller 108 includes first pulse train control 110 to control output signal driver 102 to generate a first pulse train and second pulse train control 112 to control output signal driver 102 to generate a second pulse train. The first pulse train and the second pulse train may be configured to reduce coupling with non-target motor or sensory nerves.

The output signal driver 102 is configured to generate stimulation pulses to stimulate a nerve or nerves within a patient. Output signal driver 102 may include a pulse generator and/or other suitable circuitry for generating stimulation pulses. The controller 108 is configured to control the output signal driver 102 to selectively apply between the first electrode 104 and the second electrode 106 a first pulse train and a second pulse train. In some examples, the second pulse train may be interleaved with the first pulse train. Controller 108 may include a central processing unit (CPU), microprocessor, microcontroller, application-specific integrated circuit (ASIC), and/or other suitable logic circuitry for controlling the operation of output signal driver 102. Controller 108 may include a memory storing machine-readable instructions (e.g., firmware) executed by the controller for controlling the operation of output signal driver 102. Controller 108 may operate output signal driver 102 in a voltage stimulation mode or a current stimulation mode. In the voltage stimulation mode, controller 108 may control the output signal driver 102 to apply constant voltage pulses between the first electrode 104 and the second electrode 106. In the current stimulation mode, controller 108 may control the output signal driver 102 to apply constant current pulses between the first electrode 104 and the second electrode 106.

As will be described further below with reference to FIGS. 5A-5N, in one example, the first pulse train may include a first frequency and the second pulse train may include a second frequency different from the first frequency. In another example, the first pulse train may include a first duty cycle and the second pulse train may include a second duty cycle different from the first duty cycle. In other examples, each pulse of the first pulse train may include a first pulse shape and each pulse of the second pulse train may include a second pulse shape different from the first pulse shape. The first pulse shape may include a quasi-trapezoidal pulse shape and the second pulse shape may include a square pulse shape. The first pulse shape may include a triangular pulse shape and the second pulse shape may include a square pulse shape. The first pulse shape may include a first rectangular pulse shape having a first amplitude and the second pulse shape may include a second rectangular pulse shape having a second amplitude greater than the first amplitude. In other examples, the first pulse shape and the second pulse shape may include other suitable pulse shapes.

In some examples, the first pulse train and the second pulse train are configured to provide greater spatial specificity (for more targeted delivery of stimulation to the appropriate nerve fascicles and avoidance of delivery of stimulation to off-target fascicles or nearby muscles) and greater selectivity based on nerve type, axon diameter, etc. In other examples, the first pulse train is configured to target a first nerve while the second pulse train is configured to target a second nerve. For example, the first pulse train may be configured to target the left hypoglossal nerve, while the second pulse train may be configured to target the right hypoglossal nerve. In another example, the first pulse train may be configured to target the hypoglossal nerve, while the second pulse train may be configured to target the phrenic nerve. In yet another example, the first pulse train may be configured to target the hypoglossal nerve, while the second pulse train may be configured to target the vagus nerve or the carotid sinus nerve, etc. In this way, output signal driver 102 and controller 108 may be used to target multiple nerve targets, while preventing overlapping pulses that may cause unbalanced stimulation or unintended interaction between the two phases.

Figure 1B:
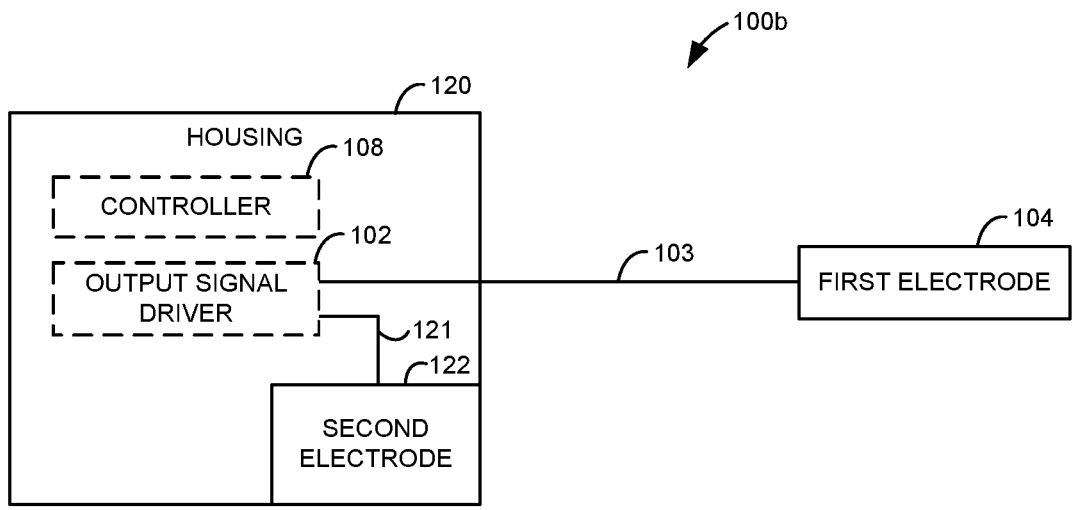

FIG. 1B is a block diagram schematically illustrating another example of an implantable medical device 100b. Implantable medical device 100b is similar to implantable medical device 100a previously described and illustrated with reference to FIG. 1A, except that implantable medical device 100b includes a second electrode 122 in place of second electrode 106. Implantable medical device 100b includes the output signal driver 102, the first electrode 104, and the controller 108 as previously described and illustrated with reference to FIG. 1A. In addition, implantable medical device 100b includes a housing 120 and a second electrode 122. Output signal driver 102 is electrically coupled to the second electrode 122 through a signal path 121. The housing 120 encloses the output signal driver 102 and the controller 108. In this example, the first electrode 104 includes a lead electrode and the second electrode 122 includes at least a portion of the housing 120. Accordingly, in this example, the second electrode 122 is distant from the first electrode 104. For example, the housing 120 may be implanted in the chest of a patient while the first electrode 104 may be implanted in the neck of the patient for delivery of UAS.

Figure 2A:
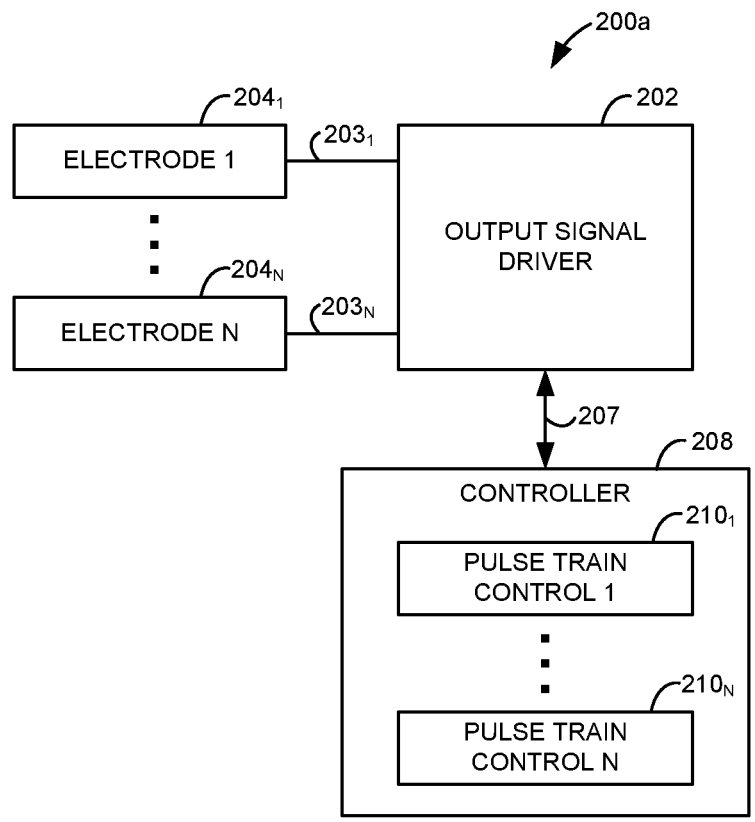
FIGS. 2A-2B are block diagrams schematically illustrating other examples of an implantable medical device.

FIG. 2A is a block diagram schematically illustrating one example of an implantable medical device 200a. Implantable medical device 200a includes an output signal driver 202, a plurality of electrodes $204_1$ to $204_N$, and a controller 208, where "N" is any suitable number of electrodes (e.g., 8). The output signal driver 202 is electrically coupled to each of the plurality of electrode $204_1$ to $204_N$ through signal paths $203_1$ to $203_N$, respectively. The output signal driver 202 is electrically coupled to the controller 208 through a signal path 207. Controller 208 includes pulse train control $210_1$ to $210_N$ for each electrode $204_1$ to $204_N$, respectively, to control output signal driver 202 to generate pulse trains (e.g., a first pulse train and a second pulse train or up to N pulse trains) between selected electrodes of the plurality of electrodes $204_1$ to $204_N$.

The output signal driver 202 is configured to generate stimulation pulses to selectively stimulate a nerve or nerves within a patient. Output signal driver 202 may include a pulse generator and/or other suitable circuitry for generating stimulation pulses. In one example, the controller 208 is configured to control the output signal driver 202 to selectively apply a first pulse train to a first set of electrodes within the plurality of electrodes $204_1$ to $204_N$ and a second pulse train to a second set of electrodes within the plurality of electrodes $204_1$ to $204_N$. In some examples, the second pulse train may be interleaved with the first pulse train. In other examples, the controller 208 is configured to control output signal driver 202 to selectively apply multiple pulse trains (e.g., up to N pulse trains) to respective multiple sets of electrodes within the plurality of electrodes $204_1$ to $204_N$. In some examples, the multiple pulse trains may be interleaved. Controller 208 may include a CPU, microprocessor, microcontroller, ASIC, and/or other suitable logic circuitry for controlling the operation of output signal driver 202. Controller 208 may include a memory storing machine-readable instructions (e.g., firmware) executed by the controller for controlling the operation of output signal driver 202. Controller 208 may operate output signal driver 202 in a voltage stimulation mode or a current stimulation mode. In the voltage stimulation mode, controller 208 controls output signal driver 202 to apply constant voltage pulses between sets of electrodes within the plurality of electrodes $204_1$ to $204_N$. In the current stimulation mode, controller 208 controls output signal driver 202 to apply constant current pulses between sets of electrodes within the plurality of electrodes $204_1$ to $204_N$.

As will be described further below with reference to FIGS. 5A-5N, in one example, each pulse of a first pulse train of multiple pulse trains (e.g., up to N pulse trains) may include a first amplitude and each pulse of a second pulse train of the multiple pulse trains may include a second amplitude different from the first amplitude. In another example, a first pulse train of multiple pulse trains may include a first frequency and a second pulse train of the multiple pulse trains may include a second frequency different from the first frequency. In another example, each pulse of a first pulse train of multiple pulse trains may include a first pulse width and each pulse of a second pulse train of the multiple pulse trains may include a second pulse width different from the first pulse width. In another example, a first pulse train of multiple pulse trains may include a first duty cycle and a second pulse train of the multiple pulse trains may include a second duty cycle different from the first duty cycle. In other examples, each pulse of a first pulse train of multiple pulse trains may include a first pulse shape and each pulse of a second pulse train of the multiple pulse trains may include a second pulse shape different from the first pulse shape. The first pulse shape may include a first amplitude and the second pulse shape may include a second amplitude different from the first amplitude. The first pulse shape may include a quasi-trapezoidal pulse shape and the second pulse shape may include a square pulse shape. The first pulse shape may include a triangular pulse shape and the second pulse shape may include a square pulse shape. The first pulse shape may include a first rectangular pulse shape having a first amplitude and the second pulse shape may include a second rectangular pulse shape having a second amplitude greater than the first amplitude. In other examples, the first pulse shape and the second pulse shape may include other suitable pulse shapes. The above described differences between a first pulse train and a second pulse train of the multiple pulse trains may be applied to the remaining pulse trains (if any) of the multiple pulse trains. In some examples, the multiple pulse trains are configured to provide greater spatial specificity (for more targeted delivery of stimulation to the appropriate nerve fascicles and avoidance of delivery of stimulation to off-target fascicles or nearby muscles) and greater selectivity based on nerve type, axon diameter, etc. In other examples, the multiple pulse trains are configured to target at least two different nerves (e.g., up to N different nerves corresponding to each pulse train of the multiple pulse trains).

As will be described further below with reference to FIGS. 3A-3C, in one example, the plurality of electrodes $204_1$ to $204_N$ are arranged in a circumferential orientation. In another example, the plurality of electrodes $204_1$ to $204_N$ are arranged in a longitudinal orientation. In yet another example, the plurality of electrodes $204_1$ to $204_N$ are arranged in a mixed circumferential and longitudinal orientation. As will be described further below with reference to FIGS. 4A-4C, the plurality of electrodes $204_1$ to $204_N$ may be arranged in a cuff.

Figure 2B:
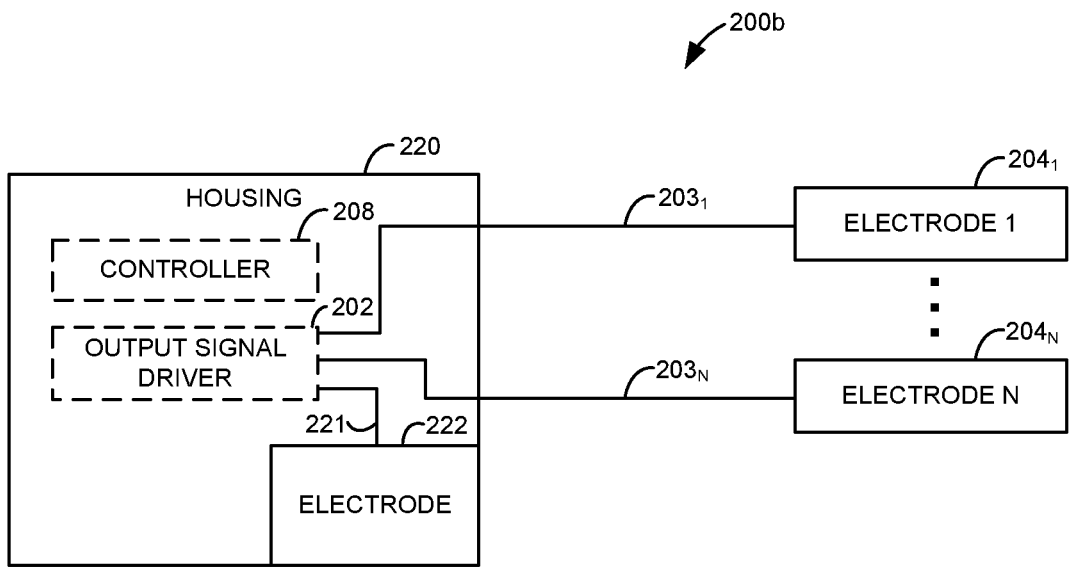

FIG. 2B is a block diagram schematically illustrating another example of an implantable medical device 200b. Implantable medical device 200b is similar to implantable medical device 200a previously described and illustrated with reference to FIG. 2A, except that implantable medical device 200b includes a further electrode 222. Implantable medical device 200b includes the output signal driver 202, the plurality of electrodes $204_1$ to $204_N$, and the controller 208 as previously described and illustrated with reference to FIG. 2A. In addition, implantable medical device 200b includes a housing 220 and a further electrode 222. Output signal driver 202 is electrically coupled to the further electrode 222 through a signal path 221. The housing 220 encloses the output signal driver 202 and the controller 208. In this example, the further electrode 222 includes at least a portion of the housing 220 and is spaced apart from the plurality of electrodes $204_1$ to $204_N$. Accordingly, in this example, the further electrode 222 is distant from the plurality of electrodes $204_1$ to $204_N$. For example, the housing 220 may be implanted in the chest of a patient while the plurality of electrodes $204_1$ to $204_N$ may be implanted in the neck of the patient for delivery of UAS.

Multiple pulse trains (e.g., a first pulse train and a second pulse train) may be applied between a single pair of electrodes (e.g., first electrode 104 and second electrode 106 or 122 of FIGS. 1A-1B) as a single burst that has nonuniform individual pulses as its constituents or may be applied between 3 or more electrodes (e.g., electrodes $204_1$ to $204_N$ and/or 222 of FIGS. 2A-2B). In some examples, two or more pairs of electrodes may form isolated stimulation circuits that drive independent pulse trains. Such pulse trains may be used to optimize UAS selectivity of recruitment of target axons and/or reduce off-target effects. Within a stimulation burst, two or more pulse shapes may be utilized, allowing different advantages of different pulse shapes to be realized. In some examples, a quasi-trapezoidal pulse anodic may be combined in some pattern (in some examples, every other pulse) with a charge-balancing cathodic square wave. In this example, stimulation is more selective for smaller versus larger diameter axons. In other examples, a triangular wave or some relatively low amplitude square wave (i.e., "DC block") may be used to modulate (up or down) the relative excitability (i.e., ease of recruitment) of different axons (based on axon diameter or distance from electrodes).

Some clinical evidence suggests that different pulse shapes may have lower activation thresholds or may have a lower likelihood of nerve fatigue. For example, a quasi-trapezoidal pulse may have a relatively low (compared to other pulse shapes) likelihood of inducing nerve fatigue. This combination (or any other combination of the pulse shapes detailed herein) of pulse shapes may be tuned for maximally effective UAS delivery (on per-patient or full-population measure).

Interleaving methods that reduce likelihood of nerve fatigue may increase flexibility in duty cycle versus existing UAS implementations. In addition to bursts of varied pulse shape, bursts of non-uniform or non-equal amplitudes may be implemented to reduce the amount of charge delivered (for patient comfort) or to selectively activate different sets of axons. Interleaved pulse bursts between separate electrode pairs may have different amplitudes to achieve a more desirable electric field and to prevent off-target effects or to optimize efficiency of recruitment.

Figure 3A:
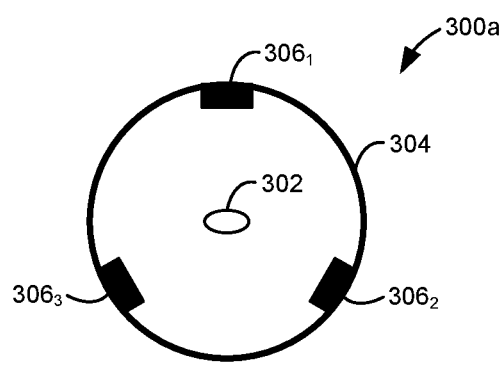
FIGS. 3A-3C are schematic diagrams illustrating examples of electrode configurations that may be used for the implantable medical devices of FIGS. 1A-2B.

FIG. 3A is a schematic diagram illustrating one example of an electrode cuff 300a that may be used in the implantable medical devices of FIGS. 1A-2B. Electrode cuff 300a includes an electrically insulating cylindrical housing 304 and a plurality of electrodes $306_1$ to $306_3$. At least one axon is indicated at 302 to illustrate the orientation of the plurality of electrodes $306_1$ to $306_3$. In this example, the plurality of electrodes $306_1$ to $306_3$ are arranged in a circumferential orientation. Thus, the plurality of electrodes $306_1$ to $306_3$ encircle the at least one axon 302. While generous spacing is shown in FIG. 3A between the axon and the electrodes $306_1$ to $306_3$ for illustrative purposes, it will be understood that the inner surface of housing 304 and the electrodes $306_1$ to $306_3$ typically are in releasable contact with an outer surface of a nerve, which includes at least one axon 302. In this example, the plurality of electrodes $306_1$ to $306_3$ includes three electrodes equally spaced circumferentially around a nerve including the at least one axon 302. In other examples, however, the plurality of electrodes may include two electrodes or more than three electrodes and the plurality of electrodes may have any suitable spacing between the electrodes. In one example, electrode cuff 300a may be used to provide the plurality of electrode $204_1$ to $204_N$ of FIGS. 2A-2B.

Figure 3B:
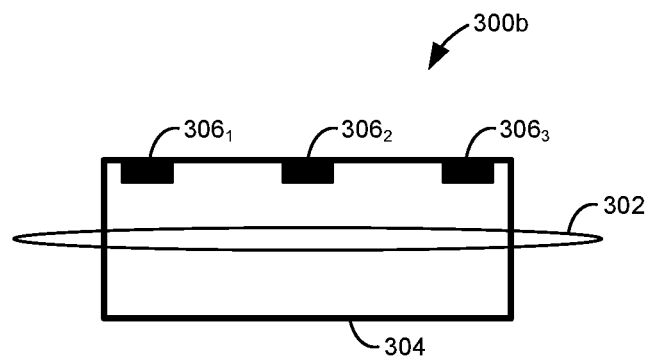

FIG. 3B is a schematic diagram illustrating another example of an electrode cuff 300b that may be used in the implantable medical devices of FIGS. 1A-2B. Electrode cuff 300b includes an electrically insulating cylindrical housing 304 and a plurality of electrodes $306_1$ to $306_3$. At least one axon is indicated at 302 to illustrate the orientation of the plurality of electrodes $306_1$ to $306_3$. In this example, the plurality of electrodes $306_1$ to $306_3$ are arranged in a longitudinal orientation. In some instances, the longitudinal orientation also may sometimes be referred to as an axial orientation. Thus, the plurality of electrodes $306_1$ to $306_3$ are aligned along one side of the at least one axon 302. As in FIG. 3A, while generous spacing is shown in FIG. 3B between the axon and the electrodes $306_1$ to $306_3$ for illustrative purposes, it will be understood that the inner surface of housing 304 and the electrodes $306_1$ to $306_3$ may be in releasable contact with an outer surface of a nerve, which includes at least one axon 302. However, in some examples the electrodes $306_1$ to $306_3$ may be spaced apart from an outer surface of the nerve (including the at least one axon) while still being able to apply a stimulation signal to the at least one axon.

In this example, the plurality of electrodes $306_1$ to $306_3$ includes three electrodes equally spaced along one side of the at least one axon 302. In other examples, however, the plurality of electrodes may include two electrodes or more than three electrodes and the plurality of electrodes may have any suitable spacing between the electrodes. In one example, electrode cuff 300b may be used to provide the plurality of electrodes $204_1$ to $204_N$ of FIGS. 2A-2B.

Figure 3C:
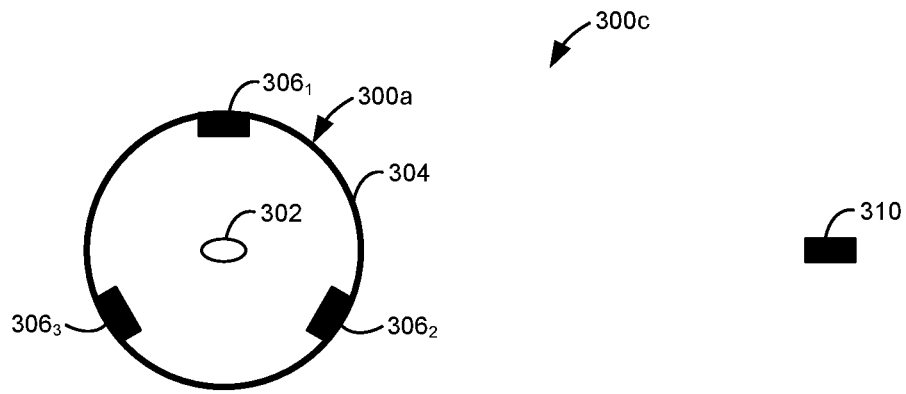

FIG. 3C is a schematic diagram illustrating another example of an electrode configuration 300c that may be used in the implantable medical devices of FIGS. 1B and 2B. In this example, electrode configuration 300c includes the electrode cuff 300a previously described and illustrated with reference to FIG. 3A and a distant electrode 310. In another example, electrode cuff 300a may be replaced with electrode cuff 300b of FIG. 3B and used in combination with distant electrode 310. In one example, distant electrode 310 may provide second electrode 122 of FIG. 1B or further electrode 222 of FIG. 2B.

In some examples, the various electrode configurations described herein are interchangeable and suited for application in UAS. Software adjustability of the stimulation mode allows accommodation of multiple electrode configurations, and the ability to swap between these electrode configurations allows greater optimization of therapy. In some examples, electrode configurations of 1-8 stimulation electrodes may be used at the stimulation site. The electrode arrangements may include circumferential, longitudinal, or mixed circumferential and longitudinal configurations. The electrode arrangements may be implemented in an electrode cuff. Electrode cuffs of different sizes with different electrode densities may be used. An increase in the number of electrodes may increase the degree of current steering attainable. Hence, the systems and methods disclosed herein accommodate a range in the number of stimulation electrodes employed. An increase in the number of electrodes also allows other options for interleaving (between one or more pairs of electrodes). The electric field that is generated by stimulation during UAS may be shaped via the physical configuration of the electrodes and a wider range of stimulation vectors may be provided.

At least some examples of the present disclosure enable greater spatial selectivity and steering current to at least some targeted nerve fascicles, which are interwoven within the motor nerves that innervate the tongue and soft palate. Accordingly, at least some examples of the present disclosure implement various electrode configurations, described previously and further described below, to provide this current steering. Additionally, current steering is achieved by shaping the electric field by applying different stimulation intensities to different stimulating electrodes. The electrodes form independent electrical interfaces between the device and the tissue and can be switched into an active or an inactive state and/or shorted to one another. Active electrodes can be used to deliver current mode (i.e., constant current) or voltage mode (i.e., constant voltage) stimulation at adjustable amplitudes and pulse shapes.

In circumferential, longitudinal, or a mixed circumferential and longitudinal electrode configurations, an electrically conductive housing or enclosure may be switched to act as an additional electrode, serving as a distant anode or cathode (e.g., 310 of FIG. 3C) and opening up options for electrical activity between the chest and neck area. For example, each of the three circumferentially arranged electrodes of 300a in FIG. 3C may source a different fraction of the total current delivered. This provides spatial specificity within the axon, allowing fascicles with therapeutic effect to be selectively recruited. The electrode configurations disclosed herein allow shaping of the electric field that is generated by stimulation during UAS via the relative proportion of the stimulation delivered via spatially-distributed electrodes as further described below with reference to FIGS. 4A-4C.

Figure 4A:
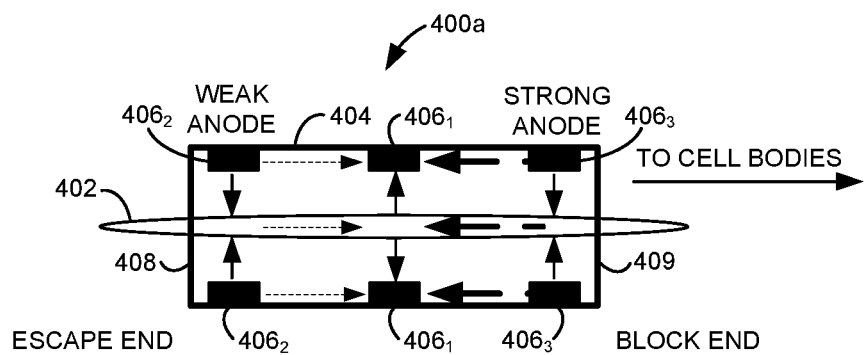
FIGS. 4A-4C are schematic diagrams illustrating other examples of electrode configurations that may be used for the implantable medical devices of FIGS. 1A-2B.

FIG. 4A is a schematic diagram illustrating another example of an electrode configuration including an electrode cuff 400a for the implantable medical devices of FIGS. 1A-2B. Electrode cuff 400a can generate unidirectional propagation of action potentials toward efferent terminals. Electrode cuff 400a is a tripolar nerve cuff electrode to which asymmetric anode stimulation intensities may be applied. Electrode cuff 400a includes an electrically insulating cylindrical housing 404, a first electrode 406$_1$, a second electrode 406$_2$, and a third electrode 406$_3$. The electrically insulating cylindrical housing 404 includes a first open end 408 and a second open end 409 opposite to the first open end 408. The electrode cuff 400a is configured to be arranged around at least one axon 402. The first electrode 406$_1$, the second electrode 406$_2$, and the third electrode 406$_3$ are within the housing 404 and attached to the sidewalls of the housing 404. The upper and lower portions of each electrode 406$_1$ to 406$_3$ illustrated in FIG. 4A may be directly electrically coupled to each other within housing 404 or may be individual electrodes electrically coupled to each other via an output signal driver, such as output signal driver 202 of FIGS. 2A-2B.

The first electrode 406$_1$ is between the second electrode 406$_2$ and the third electrode 406$_3$. The second electrode 406$_2$ is proximate the first open end 408, and the third electrode 406$_3$ is proximate the second open end 409. In this example, different electric field gradient intensities are induced (e.g., via output signal driver 202 of FIG. 2A-2B) at the first open end 408 and the second open end 409 in response to a stimulation signal applied between the first electrode 406$_1$ and the second electrode 406$_2$ and between the first electrode 406$_1$ and the third electrode 406$_3$. The stimulation signal applied between the first electrode 406$_1$ and the second electrode 406$_2$ is configured to generate greater tissue excitability toward the first open end 408, and the stimulation signal applied between the first electrode 406$_1$ and the third electrode 406$_3$ is configured to generate lesser tissue excitability toward the second open end 409. The electrode cuff 400a is configured to elicit action potentials in the direction of the first open end 408 in response to the stimulation signal.

Thus, the first open end 408 may be called the escape end and the second open end 409 may be called the block end. The block end may be proximate cell bodies where lesser tissue excitability is desired, while the escape end may be proximate the muscles or other tissues where greater tissue excitability is desired. As indicated by the relatively different sizes (e.g., thicknesses) of the arrows in FIG. 4A, the first electrode 406$_1$ may provide a cathode, the second electrode 406$_2$ may provide a weak anode, and the third electrode 406$_3$ may provide a strong anode based on the applied stimulation signal to generate the desired directionality of the elicited action potentials.

In one example, the electrode cuff 400a may be configured such that the stimulation signal selectively recruits nerve fascicles innervating a tongue and soft palate of a patient. In other examples, the electrode cuff 400a may be configured such that the stimulation signal selectively recruits nerve fascicles innervating other tissues of a patient.

Figure 4B:
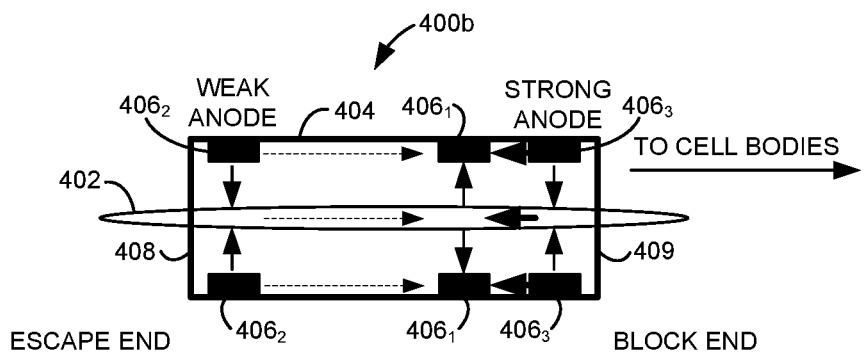

FIG. 4B is a schematic diagram illustrating another example of an electrode configuration including an electrode cuff 400b for the implantable medical devices of FIGS. 1A-2B. Electrode cuff 400b can generate unidirectional propagation of action potentials toward efferent terminals. Electrode cuff 400b is a tripolar nerve cuff electrode to which symmetric anode stimulation intensities may be applied but with a cathode closer to one anode. Electrode cuff 400b is similar to electrode cuff 400a previously described and illustrated with reference to FIG. 4A, except that in electrode cuff 400b, the first electrode 406$_1$ is closer to the second open end 409 than to the first open end 408 such that different electric field gradient intensities are induced at the first open end 408 and the second open end 409 in response to a stimulation signal applied between the first electrode 406$_1$ and the second electrode 406$_2$ and between the first electrode 406$_1$ and the third electrode 406$_3$ as previously described.

Figure 4C:
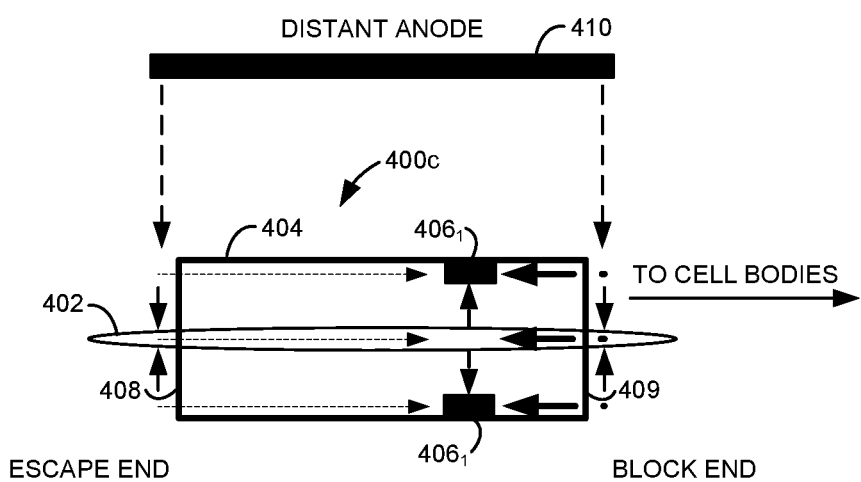

FIG. 4C is a schematic diagram illustrating another example of an electrode configuration including an electrode cuff 400c and a distant electrode 410 for the implantable medical devices of FIGS. 1A-2B. Electrode cuff 400c can generate unidirectional propagation of action potentials toward efferent terminals. Electrode cuff 400c is a monopolar nerve cuff electrode with a cathode offset along a length of the cuff electrode (note: not drawn to scale). Electrode cuff 400c includes an electrically insulating cylindrical housing 404 including a first open end 408 and a second open end 409 opposite to the first open end 408 as previously described. In this example, however, the second electrode $406_2$ and the third electrode $406_3$ are replaced with a distant electrode 410. The first electrode $406_1$ is closer to the second open end 409 than to the first open end 408 such that different electric field gradient intensities are induced at the first open end 408 and the second open end 409 in response to a stimulation signal applied between the first electrode $406_1$ and the distant electrode 410. In this example, the first electrode $406_1$ may provide a cathode and the distant electrode 410 may provide a distant anode based on the applied stimulation signal to generate the desired directionality of the elicited action potentials.

As described above with reference to FIGS. 4A-4C and as further described below, at least some examples of the present disclosure employs means of achieving directionality in elicitation of action potentials. The directionality is useful, as back propagation may lead to elicitation of undesirable muscle activity via back-propagation and elicitation of action potentials along branches proximal to the stimulation site. For UAS therapy, for example, retracting muscles (non-desirable) are usually further toward the base of the nerve, so back propagation avoidance is particularly useful.

Figure 5A:
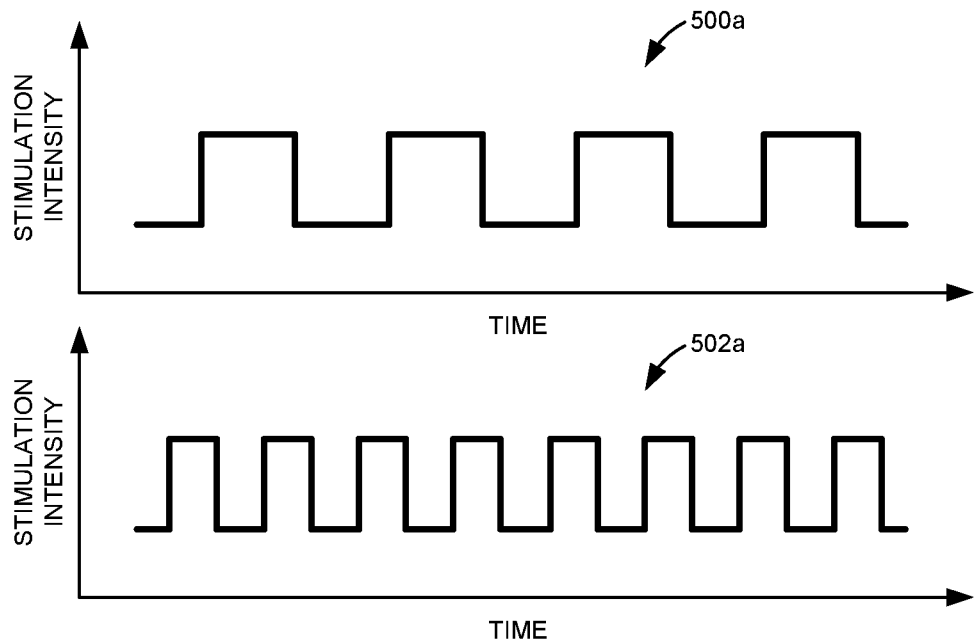
FIGS. 5A-5M are timing diagrams illustrating examples of a first pulse train and a second pulse train for stimulating a nerve or nerves within a patient.
Figure 5B:
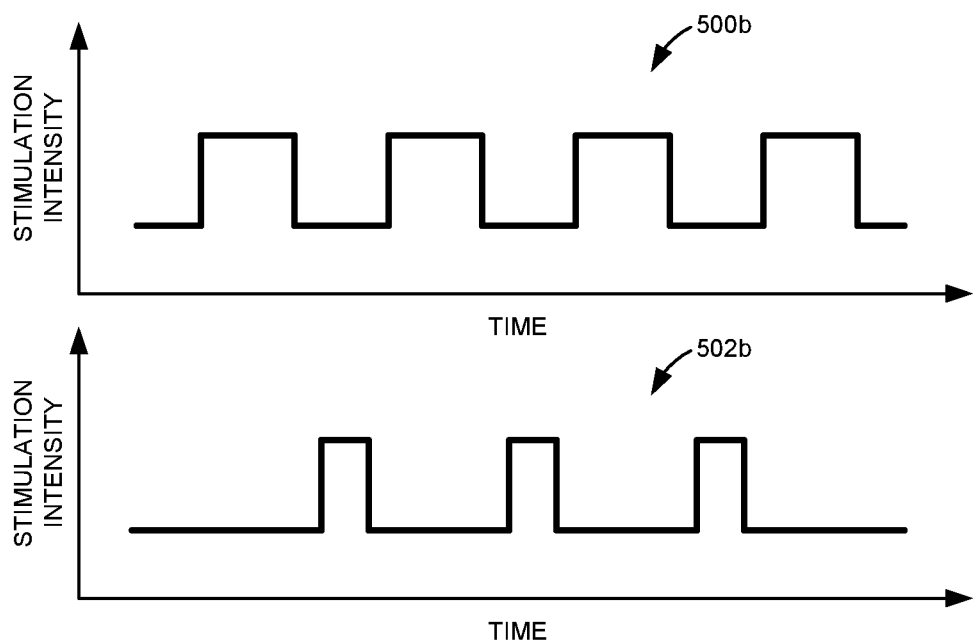
Figure 5C:
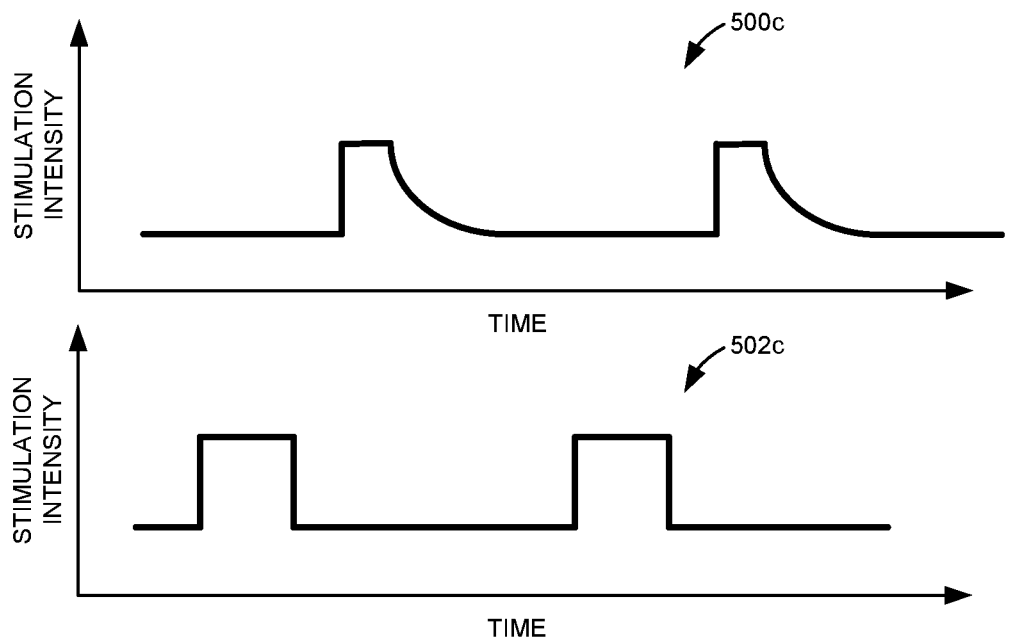
Figure 5D:
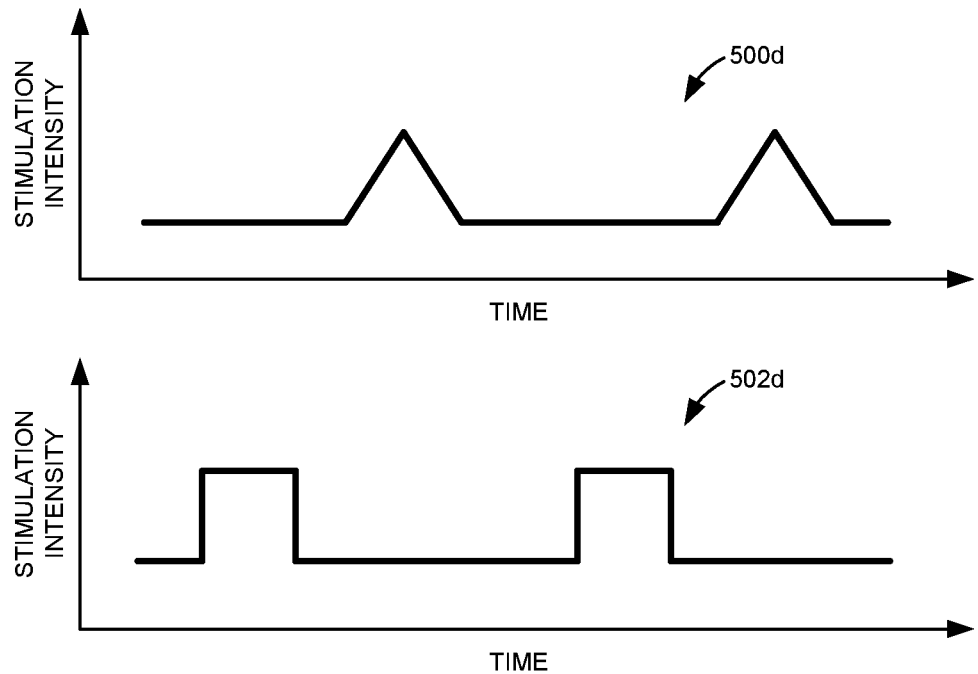
Figure 5E:
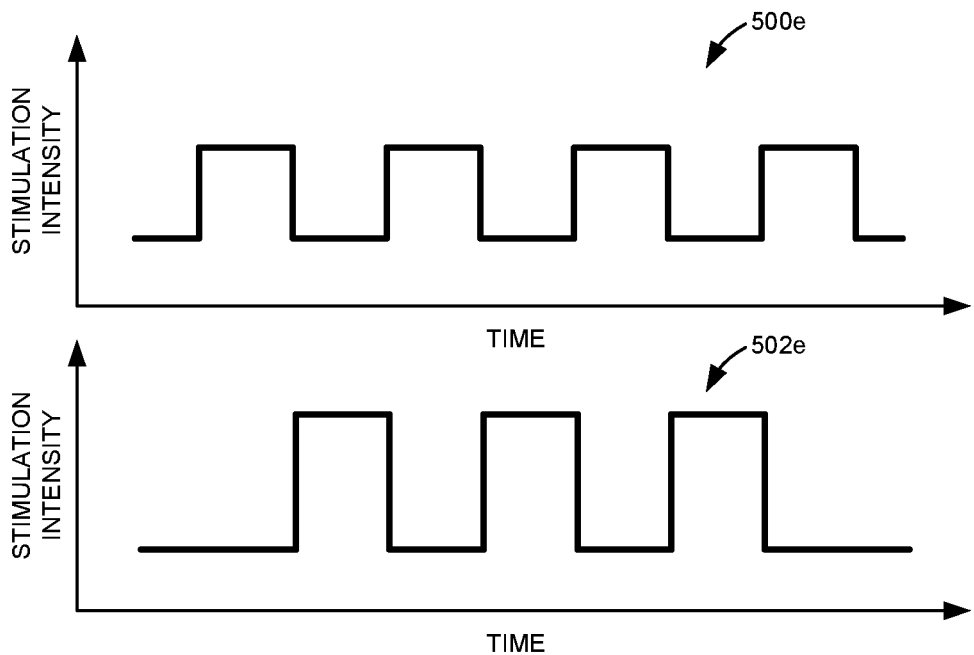
Figure 5F:
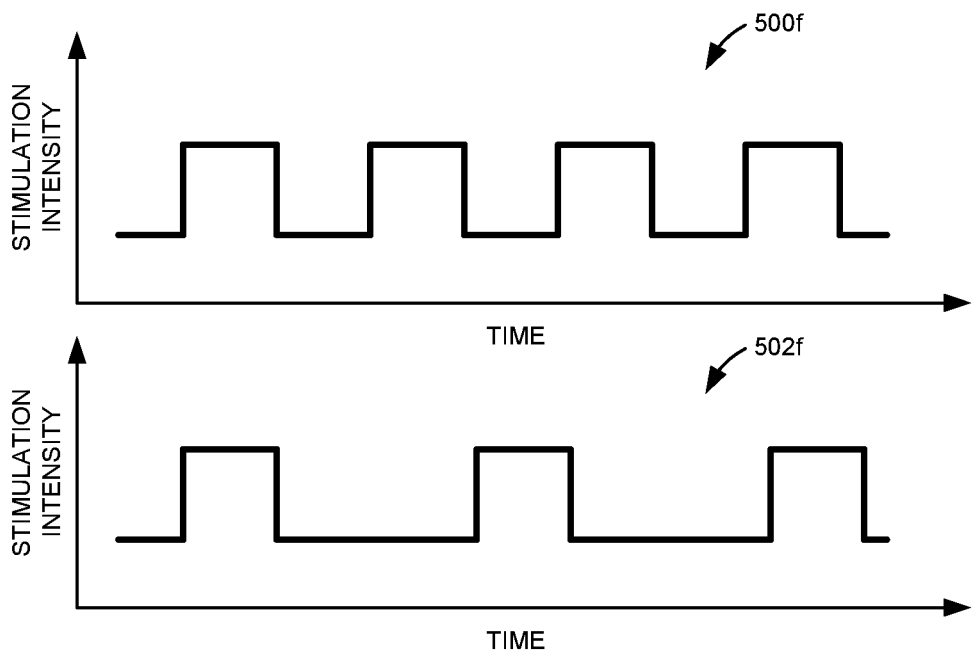
Figure 5G:
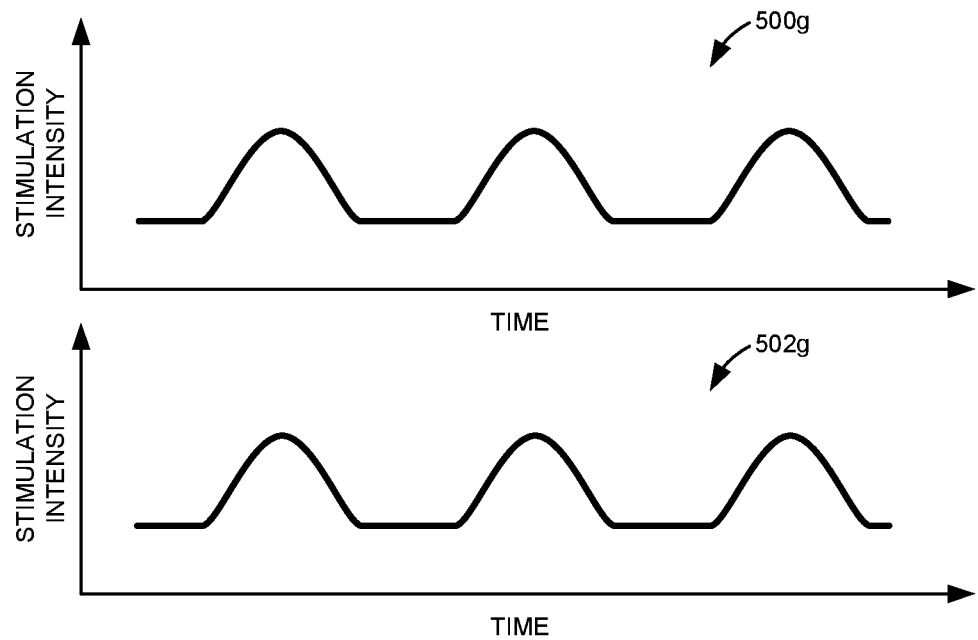
Figure 5H:
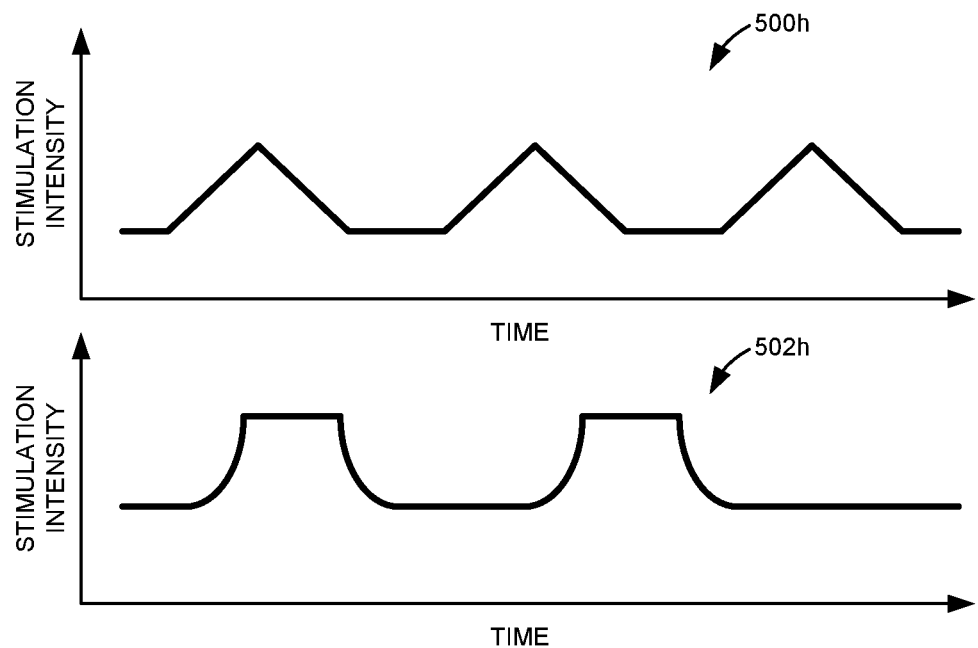
Figure 5I:
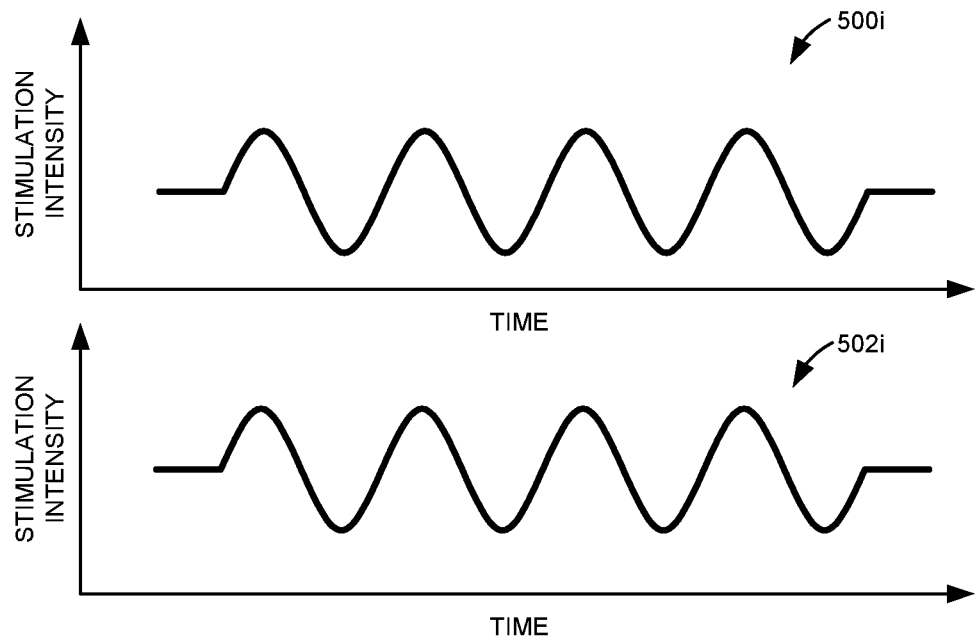
Figure 5J:
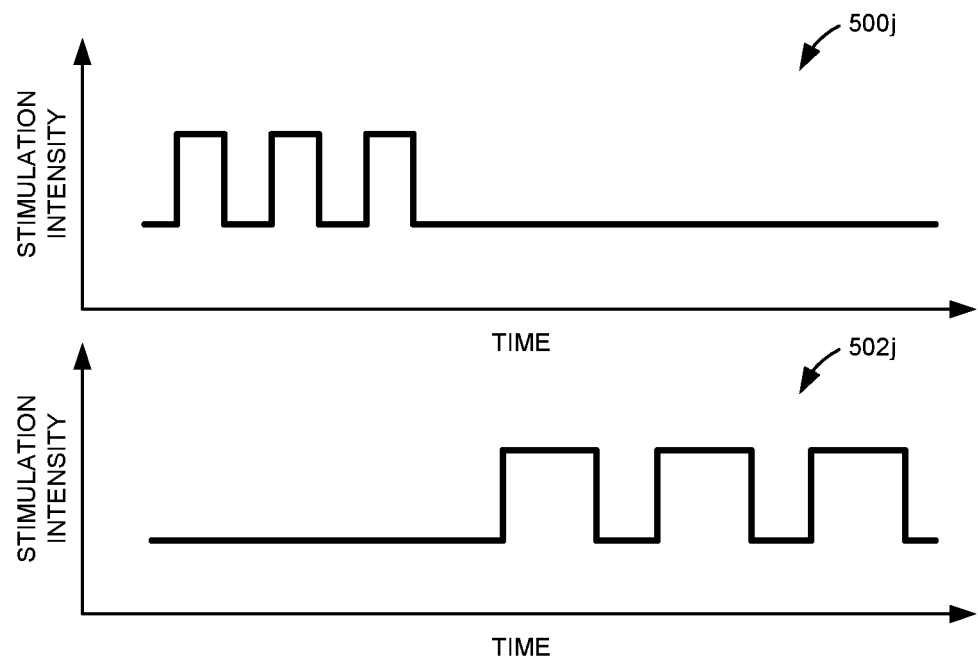

Longitudinal orientations (symmetric or nonsymmetric with two or more electrodes) may be used to achieve unidirectional elicitation of action potentials by using pre-conditioning pulses (e.g., as illustrated in FIG. 5J described below) to hyperpolarize on the side of the cuff proximal to the cell body and then, with some slight delay, using a different pair of electrodes that is further from the cell body (note: different pairs may share single electrodes, for example both may use the middle electrode of a tri-electrode cuff) to elicit action potentials that can only propagate in one direction (due to hyperpolarization block). Alternatively, symmetric cuffs of 3 or more electrodes may utilize asymmetric anode stimulation intensities to promote unidirectional propagation of action potentials.

The devices disclosed herein also accommodate the asymmetrical cuff designs previously described and illustrated with reference to FIGS. 4B and 4C, which are interchangeable and provide directionality to action potentials elicited during UAS. The FIGS. 4B and 4C present one such example of either cuff configuration, although the principle applies to other configurations. Both configurations rely on the cuff being an electrical insulator and an asymmetrical electrode configuration within the cuff driving different stimulation intensities (i.e., current or voltage) at the ends of the cuff. The result is an increased likelihood of action potentials in one direction over the other.

As detailed previously, asymmetrical current intensity can be used to shape the electric field generated along the axon. In a longitudinal electrode configuration, a central electrode will be used as cathode. A weak anode will be employed on the side closest to the target muscles and a strong anode on the side closest to the cell bodies (weak and strong anodes achieved by sourcing different intensities of stimulation). As such, action potentials are more likely to be elicited in the direction of the muscles, hence reducing the likelihood of off-target effects.

FIGS. 5A-5M are timing diagrams illustrating examples of a stimulation protocol including a first pulse train and a second pulse train for stimulating a nerve within a patient. For each example pulse train, time is indicated on the x-axis and stimulation intensity is indicated on the y-axis. The stimulation intensity indicates either a change in current (i.e., for a current stimulation mode) or a change in voltage (i.e., for a voltage stimulation mode). For each example, the first pulse train may be applied to a first electrode (e.g., first electrode 104 of FIGS. 1A-1B) or a set of electrodes (e.g., a set of electrodes within the plurality of electrodes $204_1$ to $204_N$ of FIGS. 2A-2B). For each example, the second pulse train may be applied to a second electrode (e.g., second electrode 106 of FIG. 1A, second electrode 122 of FIG. 1B, or further electrode 222 of FIG. 2B) or a set of electrodes (e.g., a set of electrodes within the plurality of electrodes $204_1$ to $204_N$ of FIGS. 2A-2B). Therefore, the first pulse train and the second pulse train may be applied across a single pathway including a first electrode and the second electrode or across different pathways including three or more electrodes.

In each example, the first pulse train may be interleaved with the second pulse train. As used herein and as illustrated in FIGS. 5A-5M, the term "interleaved" means the pulses of the first pulse train and the second pulse train are alternating, or the second pulse train immediately follows the first pulse train. In some examples, as will be described in more detail below with reference to FIGS. 5K-5M, each pulse of one pulse train may alternate with each pulse of the other pulse train (e.g., 1:1 alternating). In other examples, each pulse of one pulse train may alternate with an integer multiple "N" frequency with respect to the other pulse train (e.g., N:1 alternating). For example, ABAAAABAAAA..., which is 4:1 alternating where "A" represents a pulse from one pulse train and "B" represents a pulse of the other pulse train.

In some examples, parameters of the first pulse train and the second pulse train may be adjusted to provide greater spatial specificity (for more targeted delivery of stimulation to the appropriate nerve fascicles and avoidance of delivery of stimulation to off-target fascicles or nearby muscles) and greater selectivity based on nerve type, axon diameter, etc. In other examples, parameters of the first pulse train and the second pulse train may be adjusted to target different nerves. While FIGS. 5A-5M each illustrate two pulse trains, the described features are also applicable to embodiments including more than two pulse trains, such as up to N pulse trains as will be described below with reference to FIG. 5N.

FIG. 5A is a timing diagram illustrating one example stimulation protocol including a first pulse train 500a and a second pulse train 502a. The first pulse train 500a includes a first frequency and the second pulse train 502a includes a second frequency different from the first frequency. In this example, the second frequency is greater than the first frequency, and the pulses of the first pulse train 500a overlap with the pulses of the second pulse train 502a. While in this example, the first pulse train 500a includes 4 pulses and the second pulse train 502a includes 8 pulses, in other examples, the first pulse train 500a and the second pulse train 502a may include other suitable numbers of pulses. In addition, while the first pulse train 500a and the second pulse train 502a include rectangular pulses, in other examples, the first pulse train 500a and the second pulse train 502a may include pulses having another suitable shape, such as the pulse shapes described below with reference to FIGS. 5C, 5D, and 5G-5I.

Nerve cells possess time dynamics due to endogenous rate of firing, time constants of membrane depolarization, rates of ion exchange during repolarization, etc. In one aspect, varying frequencies of stimulation may have inhibitory or excitatory action on nerve cells, varying on the basis of nerve fiber type, nerve fiber diameter, etc. With this in mind, the stimulation timing provided in FIG. 5A provides just one example in which a higher frequency burst (e.g., pulse train 502a) may be delivered along with a baseline frequency burst (e.g., pulse train 500a) to provide a current path that captures nerves that are not the intended target of therapeutic stimulation to inhibit activity of those nerves. For instance, it may be desirable to apply such stimulation to nerves that innervate retractor muscles of the tongue to inhibit at least some retractor muscles of the tongue, while other stimulation of nerves innervating at least some protrusor muscles is left unimpeded to achieve the intended increase in upper airway patency.

FIG. 5B is a timing diagram illustrating another example stimulation protocol including a first pulse train 500b and a second pulse train 502b. Each pulse of the first pulse train 500b includes a first pulse width and each pulse of the second pulse train 502b includes a second pulse width different from the first pulse width. In this example, the second pulse width is less than the first pulse width, and the pulses of the first pulse train 500b alternate with the pulses of the second pulse train 502b. While in this example, the first pulse train 500b includes 4 pulses and the second pulse train 502b includes 3 pulses, in other examples, the first pulse train 500b and the second pulse train 502b may include other suitable numbers of pulses. In addition, while the first pulse train 500b and the second pulse train 502b include rectangular pulses, in other examples, the first pulse train 500b and the second pulse train 502b may include pulses having another suitable shape, such as the pulse shapes described below with reference to FIGS. 5C, 5D, and 5G-5I.

Via at least the example stimulation protocol of FIG. 5B, pulse width and amplitude may be varied (e.g., increased or reduced) among pulse trains to change the relative excitability of nerves. Moreover, this increase or reduction in excitability may vary from nerve to nerve for a given pulse width and amplitude due to: myelination, axon diameter (i.e., larger versus smaller diameter nerve fibers), proximity of an electrode to the stimulation target nerve, the polarity of the stimulating pulse, position relative to Nodes of Ranvier, etc. For example, relatively narrow pulse widths of 10-30 µsec may enable activation of larger diameter myelinated axons more selectively than smaller diameter axons. An interleaved pulse train, such as the interleaved pulse trains 500b, 502b of the stimulation protocol of FIG. 5B, may use one pulse train including pulses of one amplitude and pulse width to increase or decrease excitability (depending on polarity of stimulation) of the nerve and a second pulse train of a different amplitude and pulse width to elicit the desired nerve activity to cause contraction of a target muscle. One aspect of this example arrangement provides for the modulation of nerve excitability to achieve more effective or more selective nerve activation. Given the dependence of the amount of energy delivered to tissue (and, by extension, charge balancing) on pulse width and amplitude, the example arrangement depicted in FIG. 5B may be closely interrelated with those methods depicted in FIG. 5E.

FIG. 5C is a timing diagram illustrating another example stimulation protocol including a first pulse train 500c and a second pulse train 502c arranged in an interleaved pattern. Each pulse of the first pulse train 500c has a quasi-trapezoidal pulse shape and each pulse of the second pulse train 502c has a square pulse shape. In this example, the pulses of the first pulse train 500c alternate with the pulses of the second pulse train 502c. While in this example, the first pulse train 500c includes 2 pulses and the second pulse train 502c includes 2 pulses, in other examples, the first pulse train 500c and the second pulse train 502c may include other suitable numbers of pulses.

In one aspect, the example stimulation protocol of FIG. 5C provides a first pulse train 500c as having a relatively long duration pulse to hyperpolarize (and thereby reduce excitability of activation of) larger diameter nerve fibers, which enables more selective activation of smaller diameter nerve fibers, whereby activation of the smaller diameter fibers may occur due to the delivery of second pulse train 502c. As in at least some other examples, the increased selectivity provides the potential for reduced energy delivered to tissue (e.g., due to lower amplitude pulses used to elicit nerve firing) and decreased activation of non-target nerves. In one aspect, the exponential drop-off in current intensity, shown in the pulses of pulse train 500c of the example stimulation protocol of FIG. 5C, may reduce a likelihood of a phenomenon in which nerve fibers held in a hyperpolarized state (e.g., the fibers are less excitable, but with higher amplitude voltage across the membrane), are elicited to fire when a hyperpolarized state of the nerve fiber(s) is suddenly terminated. This phenomenon is due to an "over corrective" swing in membrane voltage, past baseline, that crosses the activation threshold of the nerve. However, the decaying amplitude of the trailing portion of pulse train 500c in the example stimulation protocol may reduce the rate at which the membrane (of the nerve fiber(s)) returns to a baseline state (from the hyperpolarized state), thereby reducing the likelihood of "over-corrective" firing which might otherwise occur if the hyperpolarized state was terminated abruptly.

FIG. 5D is a timing diagram illustrating another example stimulation protocol including a first pulse train 500d and a second pulse train 502d arranged in an interleaved pattern. Each pulse of the first pulse train 500d has a triangular pulse shape and each pulse of the second pulse train 502d has a square pulse shape. In this example, the pulses of the first pulse train 500d alternate with the pulses of the second pulse train 502d. While in this example, the first pulse train 500d includes 2 pulses and the second pulse train 502d includes 2 pulses, in other examples, the first pulse train 500d and the second pulse train 502d may include other suitable numbers of pulses.

In this example stimulation protocol including an interleaved pulse train, the triangular pulses of pulse train 500d may modulate the relative excitability of certain nerve fibers more or less than others. For instance, triangular and Gaussian stimulation waveforms, in particular, may exhibit a high degree of variability in effect on different types of nerve fibers on the basis of nerve fiber diameter and other characteristics of the nerve fiber. In one aspect, this phenomenon may be used to increase selectivity of stimulation of some nerve fibers, which may in turn provide the potential for reduced energy delivered to tissue (e.g., due to lower amplitude pulses used to elicit nerve firing), which thereby may result in decreased activation of non-target nerves.

FIG. 5E is a timing diagram illustrating another example stimulation protocol including a first pulse train 500e and a second pulse train 502e arranged in an interleaved pattern. Each pulse of the first pulse train 500e includes a first rectangular pulse shape having a first amplitude and each pulse of the second pulse train 502e includes a second rectangular pulse shape having a second amplitude different from the first amplitude. In this example, the second amplitude is greater than the first amplitude, and the pulses of the first pulse train 500e alternate with the pulses of the second pulse train 502e. While in this example, the first pulse train 500e includes 4 pulses and the second pulse train 502e includes 3 pulses, in other examples, the first pulse train 500e and the second pulse train 502e may include other suitable numbers of pulses. In addition, while the first pulse train 500e and the second pulse train 502e include rectangular pulses, in other examples, the first pulse train 500e and the second pulse train 502e may include pulses having another suitable shape, such as the pulse shapes described with reference to FIGS. 5C, 5D, and 5G-5I.

Via at least the example stimulation protocol of FIG. 5C, pulse width and amplitude among different pulse trains may be varied (e.g., increased or reduced) to change the relative excitability of nerves. As previously noted, this increase or reduction in excitability varies from nerve to nerve for a given pulse width and amplitude due to: myelination, axon diameter (i.e., larger versus smaller diameter nerve fibers), proximity of an electrode to the stimulation target nerve, the polarity of the stimulating pulse, position relative to Nodes of Ranvier, etc. to axon diameter, proximity to the stimulating electrodes, the polarity of the stimulating pulse, etc. Such example arrangements may use interleaved pulse widths to increase activity of nerve fibers in one region, while decreasing activity of fibers in a non-target region, which may enhance efficacious therapy. Given the dependence of the amount of energy delivered to tissue (and, by extension, charge balancing) on pulse width and amplitude, at least some aspects of the example arrangement depicted in FIG. 5B may be viewed as being closely interrelated with those methods depicted in FIG. 5B.

FIG. 5F is a timing diagram illustrating another example stimulation protocol including a first pulse train 500f and a second pulse train 502f. As shown in FIG. 5F, the first pulse train 500f includes a first duty cycle and the second pulse train 502f includes a second duty cycle different from the first duty cycle. In this example, the second duty cycle is greater than the first duty cycle, and the pulses of the first pulse train 500f overlap with the pulses of the second pulse train 502f. While in this example, the first pulse train 500f includes 4 pulses and the second pulse train 502f includes 3 pulses, in other examples, the first pulse train 500f and the second pulse train 502f may include other suitable numbers of pulses. In addition, while the first pulse train 500f and the second pulse train 502f include rectangular pulses, in other examples, the first pulse train 500f and the second pulse train 502f may include pulses having another suitable shape, such as the pulse shapes described with reference to FIGS. 5C, 5D, and 5G-5I.

In some examples, duty cycle may impact nerve fatigue, therapy effectiveness, patient comfort, etc. Via example arrangements of the present disclosure, such as the stimulation protocol of FIG. 5F, a pulse train may leverage different duty cycles at different times or along different current pathways to optimize each of these elements of therapy effectiveness and experience.

FIG. 5G is a timing diagram illustrating another example stimulation protocol including a first pulse train 500g and a second pulse train 502g. Each pulse of the first pulse train 500g has a Gaussian pulse shape and each pulse of the second pulse train 502g has a Gaussian pulse shape. In this example, the pulses of the first pulse train 500g and the pulses of the second pulse train 502g overlap and are aligned (e.g., synchronized). In other examples, the pulses of the first pulse train 500g and the pulses of the second pulse train 502g may alternate or be offset to each other. While in this example, the first pulse train 500g includes 3 pulses and the second pulse train 502g includes 3 pulses, in other examples, the first pulse train 500g and the second pulse train 502g may include other suitable numbers of pulses.

The example stimulation protocol of FIG. 5G includes the two different pulse trains 500g, 502g, by which two different current pathways may be used to increase or decrease activity along those current pathways. This arrangement may be used to increase therapy effectiveness via the recruitment of more nerve fibers, different types of nerve fibers, or nerve fibers enervating different muscle groups. Alternatively, this example arrangement may be used to increase activity in nerves (or nerve fibers) which innervate on-target muscles, but not non-target muscular or other tissue effects.

FIG. 5H is a timing diagram illustrating another example stimulation protocol including a first pulse train 500h and a second pulse train 502h. Each pulse of the first pulse train 500h has a linear rise and a linear fall (e.g., a triangular pulse shape) and each pulse of the second pulse train 502h has an exponential rise and an exponential fall. In this example, the pulses of the first pulse train 500h overlap with the pulses of the second pulse train 502h. While in this example, the first pulse train 500h includes 3 pulses and the second pulse train 502h includes 2 pulses, in other examples, the first pulse train 500h and the second pulse train 502h may include other suitable numbers of pulses.

In at least some aspects, the example stimulation protocol of FIG. 5H provides for a combination of two different types of pulse trains, each of which includes different rising and falling patterns, by which relative differences in the time dynamics of one or more nerve fibers may be leveraged for increased effectiveness and/or selectivity in nerve fiber recruitment. Stated differently, the different rising or falling shapes in the respective pulse trains 500h, 502h may be used to modulate the electric fields at or around nerve cell membranes and therefore interact with endogenous biological phenomena with a time dependence to enhance selective nerve capture, effectiveness, etc.

FIG. 5I is a timing diagram illustrating another example of a first pulse train 500i and a second pulse train 502i. The first pulse train 500i is a sinusoidal pulse train and the second pulse train 502i is a sinusoidal pulse train. In this example, the pulses of the first pulse train 500i and the pulses of the second pulse train 502i overlap and are aligned. In other examples, the pulses of the first pulse train 500i and the pulses of the second pulse train 502i may alternate or be offset to each other. While in this example, the first pulse train 500i includes 4 cycles and the second pulse train 502i includes 4 cycles, in other examples, the first pulse train 500i and the second pulse train 502i may include other suitable numbers of cycles.

FIG. 5J is a timing diagram illustrating another example of a first pulse train 500j and a second pulse train 502j. The second pulse train 502j follows the first pulse train 500j. Each pulse of the first pulse train 500j has a first pulse width and each pulse of the second pulse train 502j has a second pulse width different from the first pulse width. In this example, the first pulse width is less than the second pulse width. While in this example, the first pulse train 500j includes 3 pulses and the second pulse train 502j includes 3 pulses, in other examples, the first pulse train 500j and the second pulse train 502j may include other suitable numbers of pulses. In addition, while the first pulse train 500j and the second pulse train 502j include rectangular pulses, in other examples, the first pulse train 500j and the second pulse train 502j may include pulses having another suitable shape, such as the pulse shapes described with reference to FIGS. 5C, 5D, and 5G-5I.

Nerve cells possess time dynamics, due to endogenous rate of firing, time constants of membrane depolarization, rates of ion exchange during repolarization, etc. In one aspect, varying frequencies of stimulation may have inhibitory or excitatory action on nerve cells, varying on the basis of nerve fiber type, nerve fiber diameter, etc. With this in mind, the stimulation timing provided in FIG. 5J provides just one example in which a higher frequency burst (e.g., pulse train 500j) may be delivered along with a second slower frequency burst (e.g., pulse train 502*j*) to provide a current path that captures nerves that are not the intended target of therapeutic stimulation to inhibit activity of those nerves. For instance, it may be desirable to apply such stimulation to nerves which innervate retractor muscles of the tongue to inhibit at least some retractor muscles of the tongue while other stimulation of nerves innervating at least some protrusor muscles is left unimpeded to achieve the intended increase in upper airway patency.

Figure 5K:
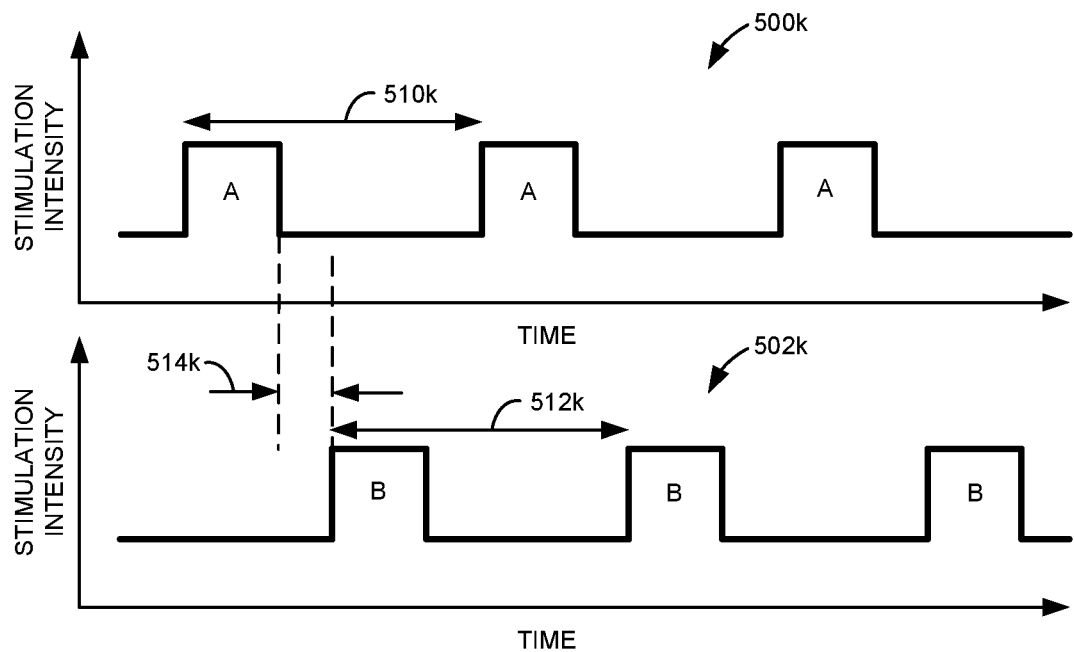

FIG. 5K is a timing diagram illustrating another example stimulation protocol including a first pulse train 500*k* and a second pulse train 502*k*. Each pulse "A" of the first pulse train 500*k* alternates with the pulses "B" of the second pulse train 502*k* in a 1:1 alternating arrangement (e.g., ABAB AB . . . ). Each pulse "A" of the first pulse train 500*k* repeats at a first rate indicated by a first interval 510*k*, and each pulse "B" of the second pulse train 502*k* repeats at a second rate indicated by a second interval 512*k*. In this example, the first rate equals the second rate such that the first interval 510*k* equals the second interval 512*k*. Each pulse "B" of the second pulse train 502*k* follows a pulse "A" of the first pulse train 500*k* by a third interval 514*k*. Third interval 514*k* may be adjusted (e.g., increased or decreased) to position each pulse "B" of the second pulse train 502*k* relative to each pulse "A" of the first pulse train 500*k*. While in this example, the first pulse train 500*k* and the second pulse train 502*k* include rectangular pulses, in other examples, the first pulse train 500*k* and the second pulse train 502*k* may include pulses having another suitable shape, such as the pulse shapes previously described with reference to FIGS. 5C, 5D, and 5G-5I. In addition, while each pulse "A" of the first pulse train 500*k* has the same pulse shape as each pulse "B" of the second pulse train 502*k*, in other examples, pulses "A" and "B" may have different shapes, including different amplitudes and/or pulse widths.

Via at least the example stimulation protocol of FIG. 5K, pulse intervals 510*k*, 512*k*, and 514*k* may be varied (e.g., increased or reduced) to change the relative excitability of nerves. Moreover, this increase or reduction in excitability may vary from nerve to nerve for given intervals due to: myelination, axon diameter (i.e., larger versus smaller diameter nerve fibers), proximity of an electrode to the stimulation target nerve, the polarity of the stimulating pulse, position relative to Nodes of Ranvier, etc. An interleaved pulse train, such as the interleaved pulse trains 500*k*, 502*k* of the stimulation protocol of FIG. 5K, may use one pulse train including pulses of one amplitude and pulse width to increase or decrease excitability (depending on polarity of stimulation) of the nerve and a second pulse train of a different amplitude and pulse width to elicit the desired nerve activity to cause contraction of a target muscle. One aspect of this example arrangement provides for the modulation of nerve excitability to achieve more effective or more selective nerve activation.

Figure 5L:
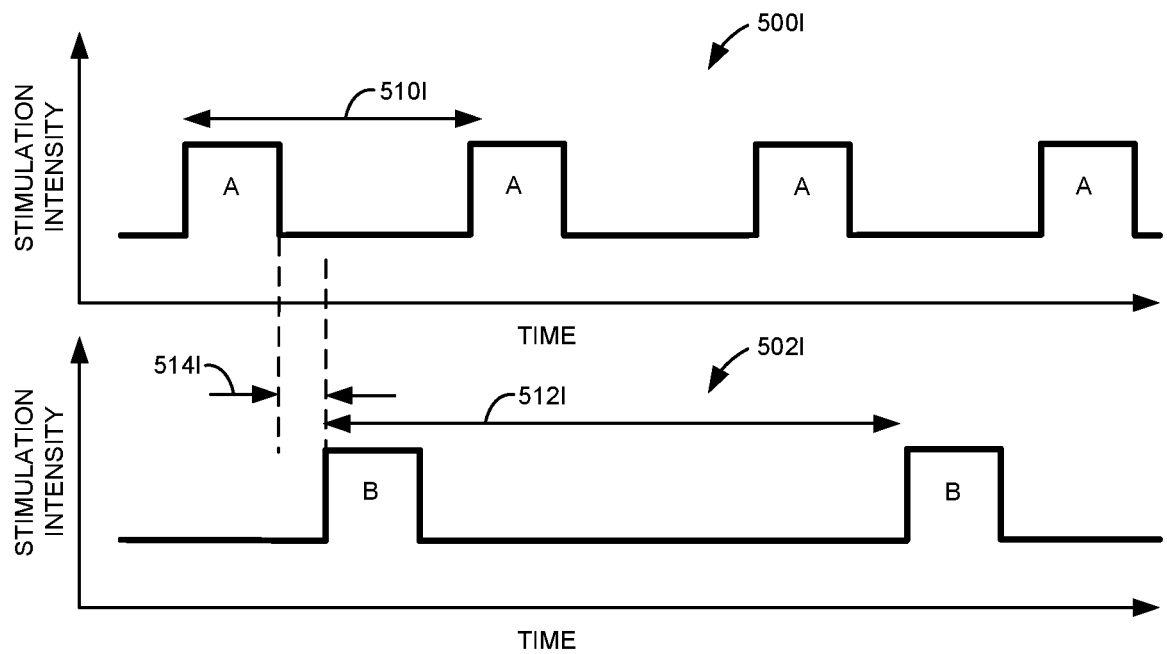

FIG. 5L is a timing diagram illustrating another example stimulation protocol including a first pulse train 500*l* and a second pulse train 502*l*. Pulses "A" of the first pulse train 500*l* alternate with the pulses "B" of the second pulse train 502*l* in a 2:1 alternating arrangement (e.g., ABAABAA . . . ). Each pulse "A" of the first pulse train 500*l* repeats at a first rate indicated by a first interval 510*l*, and each pulse "B" of the second pulse train 502*l* repeats at a second rate indicated by a second interval 512*l*. In this example, the first rate is two times the second rate such that the first interval 510*l* equals one half the second interval 512*l*. Each pulse "B" of the second pulse train 502*k* follows a pulse "A" of the first pulse train 500*k* by a third interval 514*l*. Third interval 514*l* may be adjusted (e.g., increased or decreased) to position each pulse "B" of the second pulse train 502*l* relative to a corresponding pulse "A" of the first pulse train 500*l*. While in this example, the first pulse train 500*l* and the second pulse train 502*l* include rectangular pulses, in other examples, the first pulse train 500*l* and the second pulse train 502*l* may include pulses having another suitable shape, such as the pulse shapes previously described with reference to FIGS. 5C, 5D, and 5G-5I. In addition, while each pulse "A" of the first pulse train 500*l* has the same pulse shape as each pulse "B" of the second pulse train 502*l*, in other examples, pulses "A" and "B" may have different shapes, including different amplitudes and/or pulse widths.

Via at least the example stimulation protocol of FIG. 5L, pulse intervals 510*l*, 512*l*, and 514*l* may be varied (e.g., increased or reduced) to change the relative excitability of nerves. Moreover, this increase or reduction in excitability may vary from nerve to nerve for given intervals due to: myelination, axon diameter (i.e., larger versus smaller diameter nerve fibers), proximity of an electrode to the stimulation target nerve, the polarity of the stimulating pulse, position relative to Nodes of Ranvier, etc. An interleaved pulse train, such as the interleaved pulse trains 500*l*, 502*l* of the stimulation protocol of FIG. 5I, may use one pulse train including pulses of one rate, amplitude, and pulse width to increase or decrease excitability (depending on polarity of stimulation) of the nerve and a second pulse train of a different rate, amplitude, and pulse width to elicit the desired nerve activity to cause contraction of a target muscle. One aspect of this example arrangement provides for the modulation of nerve excitability to achieve more effective or more selective nerve activation.

Figure 5M:
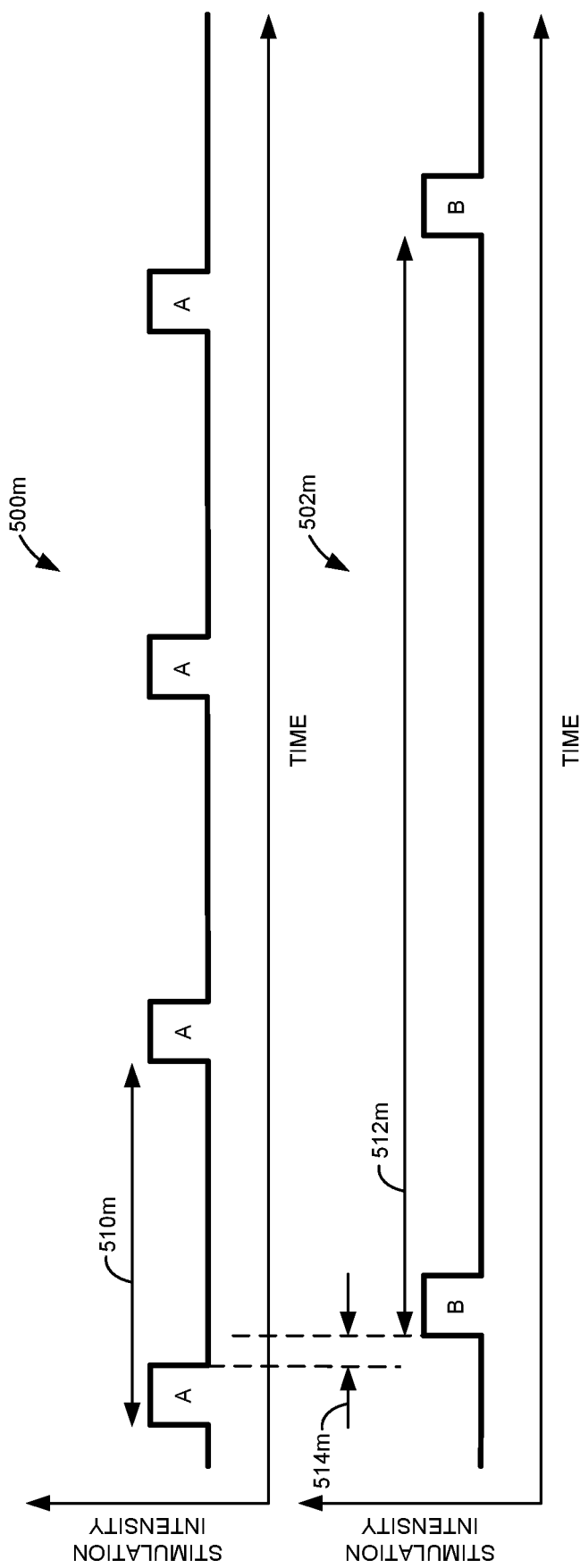

FIG. 5M is a timing diagram illustrating another example stimulation protocol including a first pulse train 500*m* and a second pulse train 502*m*. Pulses "A" of the first pulse train 500*m* alternate with the pulses "B" of the second pulse train 502*m* in a 3:1 alternating arrangement (e.g., ABAAABAAA . . . ). Each pulse "A" of the first pulse train 500*m* repeats at a first rate indicated by a first interval 510*m*, and each pulse "B" of the second pulse train 502*m* repeats at a second rate indicated by a second interval 512*m*. In this example, the first rate is three times the second rate such that the first interval 510*m* equals one third the second interval 512*m*. Each pulse "B" of the second pulse train 502*m* follows a pulse "A" of the first pulse train 500*m* by a third interval 514*m*. Third interval 514*m* may be adjusted (e.g., increased or decreased) to position each pulse "B" of the second pulse train 502*m* relative to a corresponding pulse "A" of the first pulse train 500*m*. While in this example, the first pulse train 500*m* and the second pulse train 502*m* include rectangular pulses, in other examples, the first pulse train 500*m* and the second pulse train 502*m* may include pulses having another suitable shape, such as the pulse shapes previously described with reference to FIGS. 5C, 5D, and 5G-5I. In addition, while each pulse "A" of the first pulse train 500*m* has the same pulse shape as each pulse "B" of the second pulse train 502*m*, in other examples, pulses "A" and "B" may have different shapes, including different amplitudes and/or pulse widths.

Via at least the example stimulation protocol of FIG. 5M, pulse intervals 510*m*, 512*m*, and 514*m* may be varied (e.g., increased or reduced) to change the relative excitability of nerves. Moreover, this increase or reduction in excitability may vary from nerve to nerve for given intervals due to: myelination, axon diameter (i.e., larger versus smaller diameter nerve fibers), proximity of an electrode to the stimulation target nerve, the polarity of the stimulating pulse, position relative to Nodes of Ranvier, etc. An interleaved pulse train, such as the interleaved pulse trains $500m$, $502m$ of the stimulation protocol of FIG. 5M, may use one pulse train including pulses of one rate, amplitude, and pulse width to increase or decrease excitability (depending on polarity of stimulation) of the nerve and a second pulse train of a different rate, amplitude, and pulse width to elicit the desired nerve activity to cause contraction of a target muscle. One aspect of this example arrangement provides for the modulation of nerve excitability to achieve more effective or more selective nerve activation.

While FIGS. 5K-5M illustrate three examples (e.g., 1:1 alternating, 2:1 alternating, and 3:1 alternating, respectively) where each pulse of one pulse train alternates with an integer multiple "N" frequency with respect to the other pulse train, in other examples, other N:1 alternating stimulation pulse trains may be used, such as 4:1, 5:1, 6:1, etc.

Figure 5N:
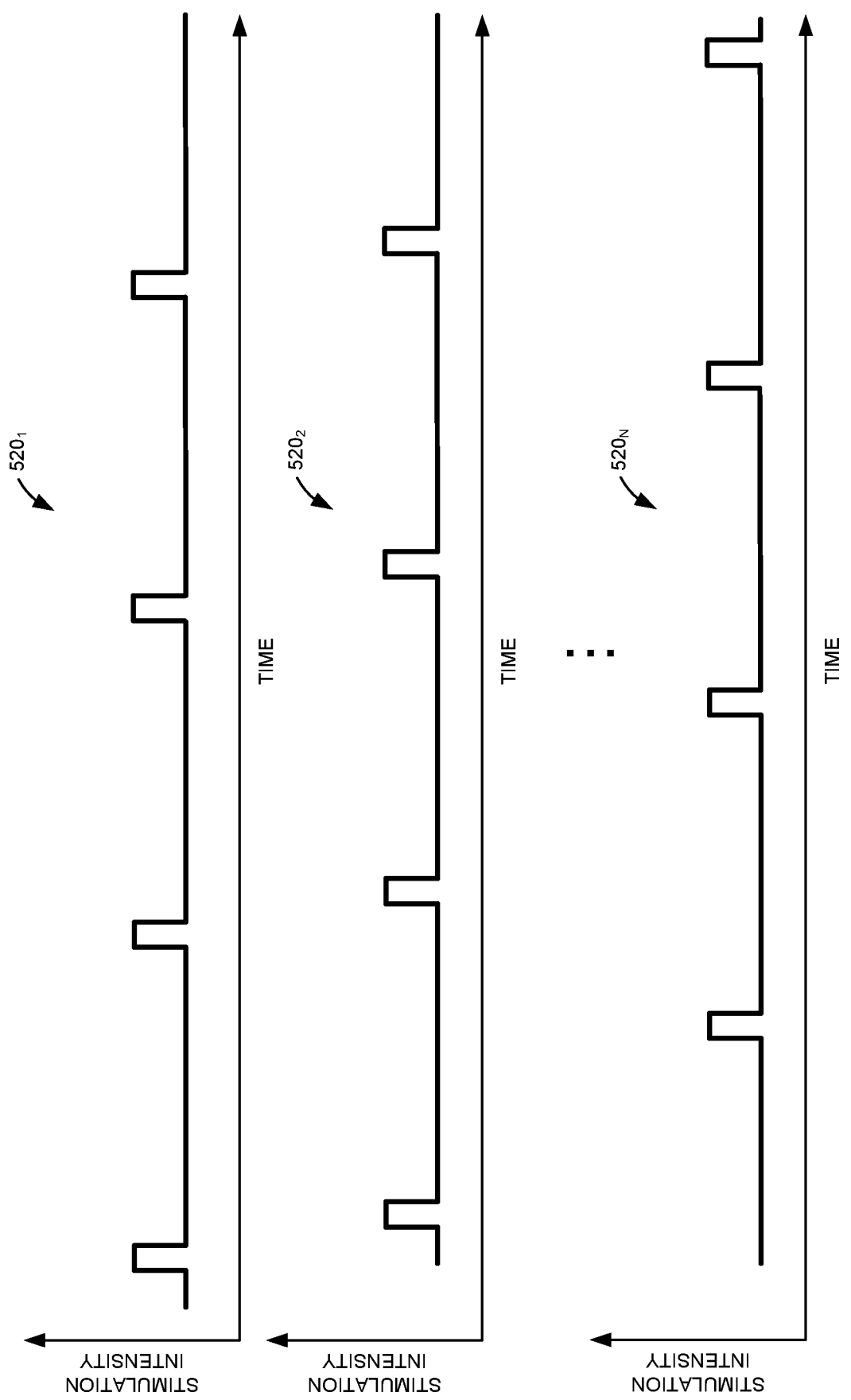
FIG. 5N is a timing diagram illustrating one example of multiple pulse trains for stimulating a nerve or nerves within a patient.

FIG. 5N is a timing diagram illustrating one example of multiple pulse trains $520_1$ to $520_N$ for stimulating a nerve or nerves within a patient. In this example, pulse trains $520_1$ to $520_N$ are interleaved such that each pulse of each pulse train $520_1$ to $520_N$ alternates with each pulse of each of the other pulse trains $520_1$ to $520_N$ (e.g., 1:1 alternating). In other examples, each pulse of each pulse train $520_1$ to $520_N$ may alternate with multiple pulses of each of the other pulse trains $520_1$ to $520_N$ (e.g., 2:1 alternating, 3:1 alternating, 4:1 alternating, etc.). Each pulse train $520_1$ to $520_N$ may include any of the features previously described and illustrated with reference to FIGS. 5A-5M.

In some examples, parameters of each pulse train $520_1$ to $520_N$ may be adjusted to provide greater spatial specificity (for more targeted delivery of stimulation to the appropriate nerve fascicles and avoidance of delivery of stimulation to off-target fascicles or nearby muscles) and greater selectivity based on nerve type, axon diameter, etc. In other examples, parameters of the of each pulse train $520_1$ to $520_N$ may be adjusted to target different nerves (e.g., up to N different nerves).

FIG. 6 is a block diagram schematically illustrating an example implantable medical device 600 in coupling relation to tissue. In some examples, the implantable medical device includes an implantable pulse generator (IPG) 602 including stimulation circuitry 610 for generating and applying a stimulation signal to tissue 630. In some examples, the tissue 630 may include a nerve 632, such as one of the types of nerves previously described for treating sleep disordered breathing, pelvic/bladder dysfunctions, cardiac issues, CNS issues, or other physiologic maladies amenable to neurostimulation therapy. In some examples, the tissue 630 may include a muscle(s) 634, the stimulation of which may provide therapeutic benefits in addition to, or instead of, nerve stimulation.

In some examples, the stimulation circuitry 610 may include at least some of substantially the same features and attributes as the examples of an output signal driver as described and illustrated in association with FIGS. 1A-5N. In some examples, the IPG 602 may be implanted within a patient's body with the stimulation circuitry 610 (e.g., at least an output signal driver) in stimulating relation to tissue 630 via coupling 620. In some examples, coupling 620 includes at least a stimulation electrode(s) 622. In some examples, the coupling 620 may include a stimulation lead having a proximal end connectable to the IPG 602 and an opposite distal end supporting the stimulation electrode(s) 622 to engage the tissue 630 or be in close proximity to the tissue 630. The IPG 602 may be implanted subcutaneously, or even percutaneously in some examples. The stimulation electrode(s) 622 may take the form of a cuff electrode, paddle electrode, or circumferential electrode, and the like, such as 300a-300c of FIGS. 3A-3C or 400a-400c of FIGS. 4A-4C. Via such arrangements, the coupling 620 (including electrode 622) includes at least an electrical connection between the IPG 602 and the tissue 630 and in some instances, also may provide a mechanical connection therebetween.

In some examples, the IPG 602 may be implemented as a microstimulator 612, which is sized and shaped for implantation in smaller anatomical spaces than a regular-sized IPG 602. Accordingly, the microstimulator 612 may be implanted transvenously, percutaneously, or subcutaneously. In some such examples, the microstimulator 612 may include a housing on which the stimulation electrode(s) 622 is provided, such that no stimulation lead is used. However, in some examples, the microstimulator 612 may be connected to a stimulation lead instead of, or in addition to, such stimulation electrode(s) 622 on the surface of the housing of the microstimulator 612.

FIG. 7A is a block diagram schematically illustrating an example control portion 700. In some examples, control portion 700 provides one example implementation of a control portion forming a part of, implementing, and/or generally managing an implantable medical device as described throughout examples of the present disclosure in association with FIGS. 1A-6. In some such examples, at least some aspects of control portion 700 may be implemented via controller 108 (FIGS. 1A-1B), controller 208 (FIGS. 2A-2B), etc.

In some examples, control portion 700 includes a controller 702 and a memory 710. In general terms, controller 702 of control portion 700 includes at least one processor 714 and associated memories. The controller 702 is electrically couplable to, and in communication with, memory 710 to generate control signals to direct operation of at least some of the stimulation elements, pulse generators, devices, user interfaces, instructions, information, elements, functions, actions, and/or methods, as described throughout examples of the present disclosure. In some examples, these generated control signals include, but are not limited to, employing instructions 711 and/or information stored in memory 710 to at least direct and manage the tasks as described throughout the examples of the present disclosure in association with FIGS. 1A-6. In some such examples, these tasks may include treatment of sleep disordered breathing such as obstructive sleep apnea and/or central sleep apnea. In some instances, the controller 702 or control portion 700 may sometimes be referred to as being programmed to perform the above-identified actions, functions, methods, etc. In some examples, at least some of the stored instructions 711 are implemented as, or may be referred to as, a task engine. In some examples, at least some of the stored instructions 711 and/or information may form at least part of, and/or, may be referred to as a task engine.

In response to or based upon commands received via a user interface (e.g., user interface 740 in FIG. 7C) and/or via machine readable instructions, controller 702 generates control signals as described above in accordance with at least some of the examples of the present disclosure. In some examples, controller 702 is embodied in a general purpose computing device while in some examples, controller 702 is incorporated into or associated with at least some of the stimulation elements, pulse generators, devices, user interfaces, instructions, information, engines, functions, actions, and/or methods, etc. as described throughout examples of the present disclosure.

For purposes of this application, in reference to the controller 702, the term "processor" shall mean a presently developed or future developed processor (or processing resources) that executes machine readable instructions contained in a memory. In some examples, execution of the machine readable instructions, such as those provided via memory 710 of control portion 700 cause the processor to perform the above-identified actions, such as operating controller 702 to implement the apnea treatment as generally described in (or consistent with) at least some examples of the present disclosure.

The machine readable instructions may be loaded in a random access memory (RAM) for execution by the processor from their stored location in a read only memory (ROM), a mass storage device, or some other persistent storage (e.g., non-transitory tangible medium or non-volatile tangible medium), as represented by memory 710. In some examples, the machine readable instructions may include a sequence of instructions, a processor-executable machine learning model, or the like. In some examples, memory 710 includes a computer readable tangible medium providing non-volatile storage of the machine readable instructions executable by a process of controller 702. In some examples, the computer readable tangible medium may sometimes be referred to as, and/or include at least a portion of, a computer program product.

In other examples, hard wired circuitry may be used in place of or in combination with machine readable instructions to implement the functions described. For example, controller 702 may be embodied as part of at least one application-specific integrated circuit (ASIC), at least one field-programmable gate array (FPGA), and/or the like. In at least some examples, the controller 702 is not limited to any specific combination of hardware circuitry and machine readable instructions, nor limited to any particular source for the machine readable instructions executed by the controller 702. In some examples, control portion 700 may be entirely implemented within or by a stand-alone device.

In some examples, the control portion 700 may be partially implemented in one of the example arrangements (or portions thereof) and partially implemented in a computing resource separate from, and independent of, the example arrangements (or portions thereof) but in communication with the example arrangements (or portions thereof). For instance, in some examples, control portion 700 may be implemented via a server accessible via the cloud and/or other network pathways. In some examples, the control portion 700 may be distributed or apportioned among multiple devices or resources, such as among a server, an implantable medical device (or portion thereof), and/or a user interface. In some examples, control portion 700 includes, and/or is in communication with, a user interface 740 as shown in FIG. 7C and described below.

FIG. 7B is a diagram schematically illustrating an example arrangement 720 of at least some example implementations by which the control portion 700 (FIG. 7A) can be implemented, according to one example of the present disclosure. In some examples, control portion 700 is entirely implemented within or by a task signal generator 725, which has at least some of substantially the same features and attributes as a pulse generator (e.g., power/control element, etc.) as previously described throughout the present disclosure. In some examples, control portion 700 is entirely implemented within or by a remote control 730 (e.g., a programmer) external to the patient's body, such as a patient control 732 and/or a clinician control 734. In some examples, at least some aspects of the control portion 700 may be implemented within a portal 736, such as a web portal. In some examples, the control portion 700 may be partially implemented in the task signal generator 725 and partially implemented in the remote control 730 (at least one of patient control 732 and physician control 734). In some examples, the remote control 730 may include a smart phone, tablet, smart watch, etc. or other mobile computing device.

FIG. 7C is a block diagram schematically illustrating user interface 740, according to one example of the present disclosure. In some examples, user interface 740 forms part of and/or is accessible via a device external to the patient and by which the therapy system may be at least partially controlled and/or monitored. The external device which hosts user interface 740 may be a patient remote (e.g., 732 in FIG. 7B), a physician remote (e.g., 734 in FIG. 7B) and/or a portal 736. In some examples, user interface 740 includes a user interface or other display that provides for the simultaneous display, activation, and/or operation of at least some of the various task elements (e.g., stimulation elements, other), task circuitry (e.g., pulse generators, other), devices, instructions, information, engines, functions, and/or methods as described in association with FIGS. 1A-6. In some examples, at least some portions or aspects of the user interface 740 are provided via a graphical user interface (GUI), and may include a display 744 and input 742.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein.

The invention claimed is:

1. An implantable medical device comprising:
   an output signal driver configured to generate stimulation pulses to stimulate a nerve within a patient;
   a first electrode coupled to the output signal driver;
   a second electrode coupled to the output signal driver; and
   a controller configured to control the output signal driver to selectively apply between the first electrode and the second electrode a first pulse train to stimulate the nerve within the patient and a second pulse train to stimulate the nerve within the patient,
   wherein the first electrode and the second electrode are arranged in an electrode cuff configured to generate unidirectional propagation of action potentials towards efferent terminals,
   wherein each pulse of the second pulse train follows a pulse of the first pulse train by an interval, and
   wherein the interval is adjustable to change the relative excitability of the nerve within the patient.

2. The implantable medical device of claim 1, wherein the first pulse train comprises a first frequency and the second pulse train comprises a second frequency different from the first frequency.

3. The implantable medical device of claim 1, wherein each pulse of the first pulse train comprises a first pulse width and each pulse of the second pulse train comprises a second pulse width different from the first pulse width.

4. The implantable medical device of claim 1, wherein the first pulse train comprises a first duty cycle and the second pulse train comprises a second duty cycle different from the first duty cycle.

5. The implantable medical device of claim 1, wherein each pulse of the first pulse train comprises a first pulse shape and each pulse of the second pulse train comprises a second pulse shape different from the first pulse shape.

6. The implantable medical device of claim 5, wherein the first pulse shape comprises a quasi-trapezoidal pulse shape and the second pulse shape comprises a square pulse shape.

7. The implantable medical device of claim 5, wherein the first pulse shape comprises a triangular pulse shape and the second pulse shape comprises a square pulse shape.

8. The implantable medical device of claim 5, wherein the first pulse shape comprises a first rectangular pulse shape having a first amplitude and the second pulse shape comprises a second rectangular pulse shape having a second amplitude greater than the first amplitude.

9. The implantable medical device of claim 1, further comprising:
 a housing enclosing the output signal driver and the controller.

10. An implantable medical device comprising:
 an output signal driver configured to generate stimulation pulses to selectively stimulate a nerve within a patient;
 a plurality of electrodes coupled to the output signal driver, wherein at least one of the plurality of electrodes is arranged in an electrode cuff configured to generate unidirectional propagation of action potentials towards efferent terminals; and
 a controller configured to control the output signal driver to selectively apply a first pulse train to a first set of electrodes within the plurality of electrodes to stimulate the nerve within the patient and a second pulse train interleaved with the first pulse train to a second set of electrodes within the plurality of electrodes to stimulate the nerve within the patient,
 wherein each pulse of the second pulse train follows a pulse of the first pulse train by an interval, and
 wherein the interval is adjustable to change the relative excitability of the nerve within the patient.

11. The implantable medical device of claim 10, wherein each pulse of the first pulse train comprises a first amplitude and each pulse of the second pulse train comprises a second amplitude different from the first amplitude.

12. The implantable medical device of claim 10, wherein the first pulse train comprises a first frequency and the second pulse train comprises a second frequency different from the first frequency.

13. The implantable medical device of claim 10, wherein each pulse of the first pulse train comprises a first pulse width and each pulse of the second pulse train comprises a second pulse width different from the first pulse width.

14. The implantable medical device of claim 10, wherein the first pulse train comprises a first duty cycle and the second pulse train comprises a second duty cycle different from the first duty cycle.

15. The implantable medical device of claim 10, wherein each pulse of the first pulse train comprises a first pulse shape and each pulse of the second pulse train comprises a second pulse shape different from the first pulse shape.

16. The implantable medical device of claim 15, wherein the first pulse shape comprises a first amplitude and the second pulse shape comprises a second amplitude different from the first amplitude.

17. The implantable medical device of claim 15, wherein the first pulse shape comprises a quasi-trapezoidal pulse shape and the second pulse shape comprises a square pulse shape.

18. The implantable medical device of claim 15, wherein the first pulse shape comprises a triangular pulse shape and the second pulse shape comprises a square pulse shape.

19. The implantable medical device of claim 15, wherein the first pulse shape comprises a first rectangular pulse shape having a first amplitude and the second pulse shape comprises a second rectangular pulse shape having a second amplitude greater than the first amplitude.

20. The implantable medical device of claim 10, wherein a burst duration of the first pulse train and the second pulse train is selectively adjusted for maximum sustained airway patency.

21. The implantable medical device of claim 10, wherein the plurality of electrodes are symmetrically arranged in the electrode cuff, and
 wherein the controller is configured to selectively select the first set of electrodes and the second set of electrodes to prevent stimulation of untargeted nerves within the patient.

22. The implantable medical device of claim 10, wherein the electrode cuff comprises a tripolar electrode cuff.

23. The implantable medical device of claim 10, wherein the electrode cuff comprises a monopolar electrode cuff.

24. An implantable medical device comprising:
 an output signal driver configured to generate stimulation pulses to stimulate a nerve within a patient;
 a first electrode coupled to the output signal driver;
 a second electrode coupled to the output signal driver; and
 a controller configured to control the output signal driver to selectively apply between the first electrode and the second electrode a first pulse train to stimulate the nerve within the patient and a second pulse train interleaved with the first pulse train to stimulate the nerve within the patient,
 wherein the first electrode and the second electrode are arranged in an electrode cuff configured to generate unidirectional propagation of action potentials towards efferent terminals,
 wherein each pulse of the second pulse train follows a pulse of the first pulse train by an interval, and
 wherein the interval is adjustable to change the relative excitability of the nerve within the patient.

25. The implantable medical device of claim 24, wherein each pulse of the first pulse train alternates with an integer multiple frequency with respect to the second pulse train.

26. The implantable medical device of claim 24, further comprising:
 a plurality of electrodes including the first electrode and the second electrode, wherein the controller is configured to control the output signal driver to selectively apply between sets of the plurality of electrodes, multiple interleaved pulse trains including the first pulse train and the second pulse train.

* * * * *